United States Patent
O'Phelan et al.

(10) Patent No.: US 8,543,201 B2
(45) Date of Patent: Sep. 24, 2013

(54) FLAT CAPACITOR HAVING STAKED FOILS AND EDGE-CONNECTED CONNECTION MEMBERS

(75) Inventors: Michael J. O'Phelan, Oakdale, MN (US); James M. Poplett, Plymouth, MN (US); Robert R. Tong, Valencia, CA (US); Rajesh Iyer, Edina, MN (US); Alexander Gordon Barr, Burnsville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 701 days.

(21) Appl. No.: 12/072,785

(22) Filed: Feb. 28, 2008

(65) Prior Publication Data

US 2008/0154319 A1 Jun. 26, 2008

Related U.S. Application Data

(62) Division of application No. 10/728,655, filed on Dec. 5, 2003, now Pat. No. 7,347,880, which is a division of application No. 09/706,518, filed on Nov. 3, 2000, now Pat. No. 6,687,118.

(51) Int. Cl.
*A61N 1/40* (2006.01)
(52) U.S. Cl.
USPC ............................ 607/5; 361/503; 361/508
(58) Field of Classification Search
USPC ...................... 361/502–522; 607/5
See application file for complete search history.

(56) References Cited

U.S. PATENT DOCUMENTS

| | | | |
|---|---|---|---|
| 1,428,399 | A | 9/1922 | Schilling |
| 1,474,486 | A | 11/1923 | Macpherson |
| 1,857,015 | A | 5/1932 | Gere |

(Continued)

FOREIGN PATENT DOCUMENTS

| | | |
|---|---|---|
| EP | 0224733 A1 | 6/1987 |
| GB | 825900 | 12/1959 |

(Continued)

OTHER PUBLICATIONS

Block, M., "Biphasic Defibrillation Using a Single Capacitor with Large Capacitance: Reduction of Peak Voltages and ICD Device Size", *PACE*, vol. 19, (Feb. 1996), 207-214.

(Continued)

*Primary Examiner* — H. Jey Tsai
(74) *Attorney, Agent, or Firm* — Schwegman Lundberg & Woessner, P.A.

(57) ABSTRACT

A method of joining a connection member to a capacitor foil using a staking tool having a tip of less than 0.030" (0.762 mm) in diameter. Another embodiment couples multiple connection members of a capacitor together by edge-connecting each connection member to its substantially flush neighboring connection members. In one aspect, a capacitor includes a multi-anode stack connected at a first weld by a weld joint less than 0.060" (1.524 mm) in diameter and a tab attached to one of the anodes of the multi-anode stack at a second weld. In one aspect, an exemplary method joining one or more foils using a staking tool having a tip of less than approximately 0.060" (1.524 mm) in diameter. In another aspect, a capacitor including a capacitor case having an electrolyte therein and a high formation voltage anode foil having a porous structure and located within the capacitor case.

19 Claims, 11 Drawing Sheets

(56) References Cited

U.S. PATENT DOCUMENTS

| | | | |
|---|---|---|---|
| 1,867,249 A | 7/1932 | Clark et al. |
| 1,895,738 A | 1/1933 | Shugg et al. |
| 1,931,043 A | 10/1933 | Taylor |
| 2,190,826 A | 2/1940 | Deeley |
| 2,203,902 A | 6/1940 | Georgiev |
| 2,555,326 A | 6/1951 | Doughty, Jr. |
| 3,150,301 A | 9/1964 | Schils et al. |
| 3,182,238 A | 5/1965 | Toder et al. |
| 3,389,311 A | 6/1968 | Rayno |
| 3,424,857 A | 1/1969 | Miller et al. |
| 3,611,055 A | 10/1971 | Zeppieri et al. |
| 3,643,168 A | 2/1972 | Manicki |
| 3,686,535 A | 8/1972 | Piper |
| 3,686,538 A | 8/1972 | Webster |
| 3,723,926 A | 3/1973 | Thomas et al. |
| 3,742,938 A | 7/1973 | Stern |
| 3,777,570 A | 12/1973 | Thomas et al. |
| 3,803,457 A | 4/1974 | Yamamoto |
| 3,818,177 A | 6/1974 | Needham et al. |
| 3,826,143 A | 7/1974 | Thomas et al. |
| 3,828,227 A | 8/1974 | Millard et al. |
| 3,852,647 A | 12/1974 | Ishii |
| 3,859,574 A | 1/1975 | Brazier |
| 3,894,210 A | 7/1975 | Smith et al. |
| 3,914,666 A | 10/1975 | Schmickl et al. |
| 3,938,228 A | 2/1976 | Kemkers et al. |
| 3,993,508 A | 11/1976 | Erlichman |
| 4,033,848 A | 7/1977 | Strempel et al. |
| 4,045,644 A | 8/1977 | Shafer et al. |
| 4,047,790 A | 9/1977 | Carino |
| 4,059,216 A | 11/1977 | Meyer |
| 4,086,148 A | 4/1978 | Badia |
| 4,088,108 A | 5/1978 | Hager |
| 4,107,022 A | 8/1978 | Strempel et al. |
| 4,113,921 A | 9/1978 | Goldstein et al. |
| 4,131,935 A | 12/1978 | Clement |
| 4,169,003 A | 9/1979 | Dangel et al. |
| 4,171,477 A | 10/1979 | Funari |
| 4,232,099 A | 11/1980 | Sullivan |
| 4,245,277 A | 1/1981 | van Gils et al. |
| 4,247,883 A | 1/1981 | Thompson et al. |
| 4,267,565 A | 5/1981 | Puppolo et al. |
| 4,296,186 A | 10/1981 | Wolf |
| 4,307,142 A | 12/1981 | Blitstein et al. |
| 4,384,188 A | 5/1983 | Wright, Jr. |
| 4,385,342 A | 5/1983 | Puppolo et al. |
| 4,394,713 A | 7/1983 | Yoshida |
| 4,425,412 A | 1/1984 | Dittmann et al. |
| 4,481,083 A | 11/1984 | Ball et al. |
| 4,539,999 A | 9/1985 | Mans |
| 4,553,304 A | 11/1985 | Fleuret |
| 4,562,511 A | 12/1985 | Nishino et al. |
| 4,571,662 A | 2/1986 | Conquest et al. |
| 4,577,257 A | 3/1986 | Erhardt et al. |
| 4,585,209 A | 4/1986 | Aine et al. |
| 4,604,260 A | 8/1986 | Shimizu et al. |
| 4,614,194 A | 9/1986 | Jones et al. |
| 4,616,655 A | 10/1986 | Weinberg et al. |
| 4,659,636 A | 4/1987 | Suzuki et al. |
| 4,664,116 A | 5/1987 | Shaya et al. |
| 4,676,879 A | 6/1987 | Salvadori |
| 4,683,516 A | 7/1987 | Miller |
| 4,745,039 A | 5/1988 | Yoshinaka |
| 4,763,229 A | 8/1988 | Ohtuka et al. |
| 4,782,340 A | 11/1988 | Czubatyj et al. |
| 4,796,638 A | 1/1989 | Sasaki |
| 4,833,719 A | 5/1989 | Carme et al. |
| 4,843,518 A | 6/1989 | Okumura |
| 4,931,899 A | 6/1990 | Pruett |
| 4,970,626 A | 11/1990 | Kakinoki et al. |
| 4,992,910 A | 2/1991 | Evans et al. |
| 5,041,942 A | 8/1991 | Carrico |
| 5,131,388 A | 7/1992 | Pless et al. |
| 5,142,439 A | 8/1992 | Huggett et al. |
| 5,173,375 A | 12/1992 | Cretzmeyer et al. |
| 5,175,067 A | 12/1992 | Taylor et al. |
| 5,195,019 A | 3/1993 | Hertz |
| 5,279,029 A | 1/1994 | Burns |
| 5,302,414 A | 4/1994 | Alkhimov et al. |
| 5,306,581 A | 4/1994 | Taylor et al. |
| 5,333,095 A | 7/1994 | Stevenson et al. |
| 5,367,437 A | 11/1994 | Anderson |
| 5,369,547 A | 11/1994 | Evans |
| 5,370,663 A | 12/1994 | Lin |
| 5,377,073 A * | 12/1994 | Fukaumi et al. ............... 361/540 |
| 5,384,685 A | 1/1995 | Tong et al. |
| 5,414,588 A | 5/1995 | Barbee, Jr. et al. |
| 5,422,200 A | 6/1995 | Hope et al. |
| 5,428,499 A | 6/1995 | Szerlip et al. |
| 5,439,760 A | 8/1995 | Howard et al. |
| 5,448,997 A | 9/1995 | Kruse et al. |
| 5,469,325 A | 11/1995 | Evans |
| 5,471,087 A | 11/1995 | Buerger, Jr. |
| 5,493,259 A | 2/1996 | Blalock et al. |
| 5,493,471 A | 2/1996 | Walther et al. |
| 5,507,966 A | 4/1996 | Liu |
| 5,522,851 A | 6/1996 | Fayram |
| 5,527,346 A | 6/1996 | Kroll |
| 5,554,178 A | 9/1996 | Dahl et al. |
| 5,559,667 A | 9/1996 | Evans |
| 5,584,890 A | 12/1996 | MacFarlane et al. |
| 5,628,801 A | 5/1997 | MacFarlane et al. |
| 5,634,938 A | 6/1997 | Swanson et al. |
| 5,640,756 A | 6/1997 | Brown et al. |
| 5,645,586 A | 7/1997 | Meltzer |
| 5,658,319 A | 8/1997 | Kroll |
| 5,660,737 A | 8/1997 | Elias et al. |
| 5,691,079 A | 11/1997 | Daugaard |
| 5,711,988 A | 1/1998 | Tsai et al. |
| 5,716,729 A | 2/1998 | Sunderland et al. |
| 5,734,546 A | 3/1998 | Kuriyama et al. |
| 5,737,181 A | 4/1998 | Evans |
| 5,738,104 A | 4/1998 | Lo et al. |
| 5,748,438 A | 5/1998 | Davis et al. |
| 5,754,394 A | 5/1998 | Evans et al. |
| 5,759,394 A | 6/1998 | Rohrbach et al. |
| 5,774,261 A | 6/1998 | Omori et al. |
| 5,776,632 A | 7/1998 | Honegger |
| 5,779,699 A | 7/1998 | Lipson |
| 5,779,891 A | 7/1998 | Andelman |
| 5,790,368 A | 8/1998 | Naito et al. |
| 5,800,724 A | 9/1998 | Habeger et al. |
| 5,800,857 A | 9/1998 | Ahmad et al. |
| 5,801,917 A | 9/1998 | Elias |
| 5,808,857 A | 9/1998 | Stevens |
| 5,811,206 A | 9/1998 | Sunderland et al. |
| 5,814,082 A | 9/1998 | Fayram et al. |
| 5,821,033 A | 10/1998 | Cromack et al. |
| 5,855,995 A | 1/1999 | Haq et al. |
| 5,867,363 A | 2/1999 | Tsai et al. |
| 5,882,362 A | 3/1999 | Muffoletto et al. |
| 5,901,867 A | 5/1999 | Mattson |
| 5,908,151 A | 6/1999 | Elias |
| 5,922,215 A | 7/1999 | Pless et al. |
| 5,926,357 A | 7/1999 | Elias et al. |
| 5,926,362 A | 7/1999 | Muffoletto et al. |
| 5,930,109 A | 7/1999 | Fishler |
| 5,949,638 A | 9/1999 | Greenwood, Jr. et al. |
| 5,950,131 A | 9/1999 | Vilmur |
| 5,963,418 A | 10/1999 | Greenwood, Jr. et al. |
| 5,968,210 A | 10/1999 | Strange et al. |
| 5,973,906 A | 10/1999 | Stevenson et al. |
| 5,980,977 A | 11/1999 | Deng et al. |
| 5,982,609 A | 11/1999 | Evans |
| 5,983,472 A | 11/1999 | Fayram et al. |
| 6,002,969 A | 12/1999 | Machek et al. |
| 6,004,692 A | 12/1999 | Muffoletto et al. |
| 6,006,133 A | 12/1999 | Lessar et al. |
| 6,009,348 A | 12/1999 | Rorvick et al. |
| 6,030,480 A | 2/2000 | Face, Jr. et al. |
| 6,032,075 A | 2/2000 | Pignato et al. |
| 6,040,082 A | 3/2000 | Haas et al. |
| 6,042,624 A | 3/2000 | Breyen et al. |
| 6,052,625 A | 4/2000 | Marshall |

| Patent No. | Date | Inventor |
|---|---|---|
| 6,076,014 A | 6/2000 | Alt |
| 6,094,339 A | 7/2000 | Evans |
| 6,094,788 A | 8/2000 | Farahmandi et al. |
| 6,099,600 A | 8/2000 | Yan et al. |
| 6,104,961 A | 8/2000 | Conger et al. |
| 6,110,233 A | 8/2000 | O'Phelan et al. |
| 6,110,321 A | 8/2000 | Day et al. |
| 6,117,194 A | 9/2000 | Strange et al. |
| 6,118,651 A | 9/2000 | Mehrotra, V et al. |
| 6,118,652 A | 9/2000 | Casby et al. |
| 6,139,986 A | 10/2000 | Kurokawa et al. |
| 6,141,205 A | 10/2000 | Nutzman et al. |
| 6,157,531 A | 12/2000 | Breyen et al. |
| 6,162,264 A | 12/2000 | Miyazaki et al. |
| 6,184,160 B1 | 2/2001 | Yan et al. |
| 6,191,931 B1 | 2/2001 | Paspa et al. |
| 6,204,476 B1 | 3/2001 | Reynolds et al. |
| 6,212,063 B1 | 4/2001 | Johnson et al. |
| 6,225,778 B1 | 5/2001 | Hayama et al. |
| 6,249,423 B1 | 6/2001 | O'Phelan et al. |
| 6,249,709 B1 | 6/2001 | Conger et al. |
| 6,256,542 B1 | 7/2001 | Marshall et al. |
| 6,257,267 B1 | 7/2001 | Saijo et al. |
| 6,259,954 B1 | 7/2001 | Conger et al. |
| 6,275,371 B1 | 8/2001 | Yoshio et al. |
| 6,275,372 B1 | 8/2001 | Vassallo et al. |
| 6,275,729 B1 | 8/2001 | O'Phelan et al. |
| 6,283,985 B1 | 9/2001 | Harguth et al. |
| 6,297,943 B1 | 10/2001 | Carson |
| 6,299,752 B1 | 10/2001 | Strange et al. |
| 6,321,114 B1 | 11/2001 | Nutzman et al. |
| 6,324,049 B1 | 11/2001 | Inagawa et al. |
| 6,326,587 B1 | 12/2001 | Cardineau et al. |
| 6,330,925 B1 | 12/2001 | Ovshinsky et al. |
| 6,343,004 B1 * | 1/2002 | Kuranuki et al. ............ 361/523 |
| 6,375,688 B1 | 4/2002 | Akami et al. |
| 6,380,577 B1 | 4/2002 | Cadwallader |
| 6,388,284 B2 | 5/2002 | Rhodes et al. |
| 6,388,866 B1 | 5/2002 | Rorvick et al. |
| 6,402,793 B1 | 6/2002 | Miltich et al. |
| 6,404,619 B1 | 6/2002 | Marshall et al. |
| 6,409,776 B1 | 6/2002 | Yan et al. |
| 6,413,283 B1 | 7/2002 | Day et al. |
| 6,421,226 B1 | 7/2002 | O'Phelan et al. |
| 6,426,864 B1 | 7/2002 | O'Phelan et al. |
| 6,442,015 B1 | 8/2002 | Niiori et al. |
| 6,445,948 B1 | 9/2002 | Somdahl et al. |
| 6,451,073 B1 | 9/2002 | Farahmandi et al. |
| 6,459,566 B1 | 10/2002 | Casby et al. |
| 6,477,037 B1 | 11/2002 | Nielsen et al. |
| 6,477,404 B1 | 11/2002 | Yonce et al. |
| 6,493,212 B1 * | 12/2002 | Clarke et al. ................ 361/521 |
| 6,509,588 B1 | 1/2003 | O'Phelan et al. |
| 6,522,525 B1 | 2/2003 | O'Phelan et al. |
| 6,555,945 B1 | 4/2003 | Baughman et al. |
| 6,556,863 B1 | 4/2003 | O'Phelan et al. |
| 6,571,126 B1 | 5/2003 | O'Phelan et al. |
| 6,585,152 B2 | 7/2003 | Farahmandi et al. |
| 6,628,505 B1 | 9/2003 | Andelman |
| 6,631,072 B1 | 10/2003 | Paul et al. |
| 6,674,634 B2 | 1/2004 | O'Phelan et al. |
| 6,684,102 B1 | 1/2004 | O'Phelan et al. |
| 6,687,118 B1 | 2/2004 | O'Phelan et al. |
| 6,699,265 B1 | 3/2004 | O'Phelan et al. |
| 6,709,946 B2 | 3/2004 | O'Phelan et al. |
| 6,736,956 B1 | 5/2004 | Hemphill et al. |
| 6,763,265 B2 | 7/2004 | O'Phelan et al. |
| 6,795,729 B1 | 9/2004 | Breyen et al. |
| 6,833,987 B1 | 12/2004 | O'Phelan |
| 6,885,548 B2 | 4/2005 | Nyberg |
| 6,885,887 B2 | 4/2005 | O'Phelan et al. |
| 6,957,103 B2 | 10/2005 | Schmidt et al. |
| 6,985,351 B2 | 1/2006 | O'Phelan et al. |
| 6,990,375 B2 | 1/2006 | Kloss et al. |
| 6,999,304 B2 | 2/2006 | Schmidt et al. |
| 7,072,713 B2 | 7/2006 | O'Phelan et al. |
| 7,079,897 B2 | 7/2006 | Sun et al. |
| 7,107,099 B1 | 9/2006 | O'Phelan et al. |
| 7,120,008 B2 | 10/2006 | Sherwood |
| 7,154,739 B2 | 12/2006 | O'Phelan |
| 7,157,671 B2 | 1/2007 | O'Phelan et al. |
| 7,177,692 B2 | 2/2007 | O'Phelan et al. |
| 7,180,727 B2 | 2/2007 | Poplett |
| 7,190,569 B2 | 3/2007 | O'Phelan et al. |
| 7,190,570 B2 | 3/2007 | Schmidt et al. |
| 7,206,191 B2 | 4/2007 | Sherwood et al. |
| 7,221,556 B2 | 5/2007 | Schmidt et al. |
| 7,224,575 B2 | 5/2007 | Sherwood |
| 7,347,880 B2 | 3/2008 | O'Phelan et al. |
| 7,355,841 B1 | 4/2008 | Schmidt et al. |
| 7,365,960 B2 | 4/2008 | O'Phelan et al. |
| 7,443,652 B2 | 10/2008 | Sherwood |
| 7,456,077 B2 | 11/2008 | Sherwood et al. |
| 7,554,791 B2 | 6/2009 | Sherwood et al. |
| 7,576,973 B2 | 8/2009 | Schmidt et al. |
| 7,768,772 B2 | 8/2010 | Doffing et al. |
| 2001/0020319 A1 | 9/2001 | Farahmandi et al. |
| 2003/0030969 A1 | 2/2003 | Farahmandi et al. |
| 2003/0072124 A1 | 4/2003 | O'Phelan et al. |
| 2003/0077509 A1 | 4/2003 | Probst et al. |
| 2003/0165744 A1 | 9/2003 | Schubert et al. |
| 2003/0195568 A1 | 10/2003 | O'Phelan et al. |
| 2004/0019268 A1 | 1/2004 | Schmidt et al. |
| 2004/0032698 A1 | 2/2004 | Paul et al. |
| 2004/0039421 A1 | 2/2004 | O'Phelan et al. |
| 2004/0114311 A1 | 6/2004 | O'Phelan et al. |
| 2004/0127952 A1 | 7/2004 | O'Phelan et al. |
| 2004/0147960 A1 | 7/2004 | O'Phelan et al. |
| 2004/0147961 A1 | 7/2004 | O'Phelan et al. |
| 2004/0173835 A1 | 9/2004 | Schmidt et al. |
| 2004/0174658 A1 | 9/2004 | O'Phelan et al. |
| 2004/0193221 A1 | 9/2004 | O'Phelan et al. |
| 2004/0215281 A1 | 10/2004 | O'Phelan et al. |
| 2004/0220627 A1 | 11/2004 | Crespi et al. |
| 2005/0010253 A1 | 1/2005 | O'Phelan et al. |
| 2005/0017888 A1 | 1/2005 | Sherwood et al. |
| 2005/0052825 A1 | 3/2005 | O'Phelan |
| 2005/0221171 A1 | 10/2005 | Haasl et al. |
| 2006/0009808 A1 | 1/2006 | Schmidt et al. |
| 2006/0012942 A1 | 1/2006 | Poplett |
| 2006/0023400 A1 | 2/2006 | Sherwood |
| 2006/0107506 A1 | 5/2006 | Doffing et al. |
| 2006/0152887 A1 | 7/2006 | Schmidt et al. |
| 2006/0174463 A1 | 8/2006 | O'Phelan et al. |
| 2006/0179626 A1 | 8/2006 | Poplett |
| 2006/0247715 A1 | 11/2006 | Youker |
| 2006/0257726 A1 | 11/2006 | Kelley et al. |
| 2007/0118182 A1 | 5/2007 | O'Phelan |
| 2008/0030928 A1 | 2/2008 | Schmidt et al. |
| 2009/0059472 A1 | 3/2009 | Sherwood et al. |

FOREIGN PATENT DOCUMENTS

| | | |
|---|---|---|
| GB | 2132019 | 6/1984 |
| JP | 52-004051 | 1/1977 |
| JP | 59-083772 | 5/1984 |
| JP | 05-074664 | 3/1993 |
| JP | 2002-231582 | 8/2002 |
| WO | WO-98/27562 | 6/1998 |
| WO | WO-9854739 A1 | 12/1998 |
| WO | WO-99/05749 A1 | 2/1999 |
| WO | WO-99/51302 | 10/1999 |
| WO | WO-99/51302 A1 | 10/1999 |
| WO | WO-99/66985 | 12/1999 |
| WO | WO-00/19470 A1 | 4/2000 |
| WO | WO-02/37515 A2 | 5/2002 |
| WO | WO-0237515 A2 | 5/2002 |
| WO | WO-2006/002148 A1 | 1/2006 |

OTHER PUBLICATIONS

Block, M., "Internal Defibrillation with Smaller Capacitors: A Prospective Randomized Cross-Over Comparison of Defibrillation Efficacy Obtained with 90-μF and 125-μF Capacitors in Humans", *Journal of Cardiovascular Electrophysiology*, 6(5), (May 1995), 333-342.

Brugada, J., "Clinical evaluation of defibrillation efficacy with a new single-capacitor biphasic waveform in patients undergoing implantation of an implantable cardioverter defibrillator", *The European Society of Cardiology*, vol. 3, (Oct. 2001), 278-284.

Doffing, B., et al., "Method and Apparatus for Providing Flexible Partially Etched Capacitor Electrode Interconnect", U.S. Appl. No. 10/996,903, filed Nov. 24, 2004, 239 Pgs.

Hahn, S. J., et al., "Large Capacitor Defibrillation Waveform Reduces Peak Voltages without Increasing Energies", *PACE*, 18(Part II), (Jan. 1995), 203-207.

Morley, A. R., et al., "Electrolytic capacitors: their fabrication and the interpretation of their operations behaviour", *The Radio and Electronic Engineer*, 43(7),(Jul. 1973), 421-429.

Moynihan, J. D., "Theory, Design and Application of Electrolytic Capacitors", *Theory, Design and Application of Electrolytic Capacitors*Copyright by John D. Moynihan,(1982), 139 pgs.

O'Phelan, M. J., et al., "Capacitor Having a Feedthrough Assembly With a Coupling Member", U.S. Appl. No. 09/706,579, filed Nov. 3, 2000, 29 pgs.

O'Phelan, M., et al., "Capacitor Having a Feedthrough Assembly With a Coupling Member", U.S. Appl. No. 10/846,805, filed May 14, 2004, 39 pgs.

O'Phelan, M. J., et al., "Flat Capacitor for an Implantable Medical Device", U.S. Appl. No. 10/758,677, filed Jan. 15, 2004, 219 pgs.

O'Phelan, M. J., et al., "Flat Capacitor for an Implantable Medical Device", U.S. Appl. No. 10/758,701, filed Jan. 15, 2004, 219 pgs.

O'Phelan, M. J., "Flat Capacitor Having an Active Case", U.S. Appl. No. 09/706,517, filed Nov. 3, 2000, 39 pgs.

O'Phelan, M. J., "Flat Capacitor Having an Active Case", U.S. Appl. No. 10/969,441, filed Oct. 20, 2004, 44 pgs.

O'Phelan, M. J., et al., "Implantable Heart Monitors Having Capacitors With Endcap Headers", U.S. Appl. No. 10/736,209, filed Dec. 15, 2003, 19 pgs.

O'Phelan, M. J., et al., "Implantable Heart Monitors Having Flat Capacitors With Curved Profiles", U.S. Appl. No. 10/729,424, filed Dec. 4, 2003, 28 pgs.

O'Phelan, M., et al., "Method for Interconnecting Anodes and Cathodes in a Flat Capacitor", U.S. Appl. No. 10/874,798, filed Jun. 23 2004, 39 pgs.

O'Phelan, M., et al., "Method of Constructing a Capacitor Stack for a Flat Capacitor", U.S. Appl. No. 10/882,144, filed Jun. 30, 2004, 57 pgs.

Poplett, J. M., "Capacitor With Single Sided Partial Etch and Stake", U.S. Appl. No. 11/065,873, filed Feb. 25, 2005, 28 pgs.

Porter, M. C., *Handbook of Industrial Membrane Technology*, Noyes Publications, (1990), 623 pgs.

Schmidt, B. L., et al., "Configurations and Methods for Making Capacitor Connections", U.S. Appl. No. 09/706/576, filed Nov. 3, 2000, 26 pgs.

Schmidt, B. L., et al., "Method for Interconnecting Anodes and Cathodes in a Flat Capacitor", U.S. Appl. No. 10/804,288, filed Mar. 18 2004, 40 pgs.

Schmidt, B., et al., "Method for Interconnecting Anodes and Cathodes in a Flat Capacitor", U.S. Appl. No. 11/325,931, filed Jan. 5, 2006, 28 Pages.

Shams, A. M., et al., "Titanium hydride formation from Arabian Gulf water", Desalination, vol. 107, (1996),265-276.

"U.S. Appl. No. 09/706,518, Non-Final Office Action mailed Mar. 24, 2003", 7 pgs.

"U.S. Appl. No. 09/706,518, Non-Final Office Action mailed Apr. 18, 2002", 10 pgs.

"U.S. Appl. No. 09/706,518, Non-Final Office Action mailed Oct. 4, 2002", 7 pgs.

"U.S. Appl. No. 09/706,518, Notice of Allowance mailed Sep. 9, 2003", 9 pgs.

"U.S. Appl. No. 09/706,518, Response filed Jan. 6, 2003 to Non Final Office Action mailed Oct. 4, 2002", 4 pgs.

"U.S. Appl. No. 09/706,518, Response filed Jun. 24, 2003 to Non Final Office Action mailed Mar. 24, 2003", 9 pgs.

"U.S. Appl. No. 09/706,518, Response filed Jul. 18, 2002 to Non Final Office Action mailed Apr. 18, 2002", 7 pgs.

"U.S. Appl. No. 09/706,518, Response filed Nov. 30, 2001 to Restriction Requirement mailed Nov. 1, 2001", 1 pg.

"U.S. Appl. No. 09/706,518, Restriction Requirement mailed Nov. 1, 2001", 6 pgs.

"U.S. Appl. No. 10/728,655, Advisory Action mailed Apr. 16, 2007", 3 pgs.

"U.S. Appl. No. 10/728,655, Advisory Action mailed Jul. 8, 2005", 3 pgs.

"U.S. Appl. No. 10/728,655, Appeal Brief filed Jul. 31, 2007", 18 pgs.

"U.S. Appl. No. 10/728,655, Final Office Action mailed Jan. 31, 2007", 12 pgs.

"U.S. Appl. No. 10/728,655, Final Office Action mailed Apr. 5, 2005", 9 pgs.

"U.S. Appl. No. 10/728,655, Non-Final Office Action mailed Mar. 20, 2006", 10 pgs.

"U.S. Appl. No. 10/728,655, Non-Final Office Action mailed Aug. 25, 2004", 9 pgs.

"U.S. Appl. No. 10/728,655, Non-Final Office Action mailed Aug. 30, 2006", 10 pgs.

"U.S. Appl. No. 10/728,655, Non-Final Office Action mailed Sep. 21, 2005", 7 pgs.

"U.S. Appl. No. 10/728,655, Notice of Allowance mailed Oct. 24, 2007", 4 pgs.

"U.S. Appl. No. 10/728,655, Response filed Jan. 25, 2005 to Non-Final Office Action mailed Aug. 25, 2004", 14 pgs.

"U.S. Appl. No. 10/728,655, Response filed Apr. 2, 2007 to Final Office Action mailed Jan. 31, 2007", 11 pgs.

"U.S. Appl. No. 10/728,655, Response filed May 31, 2007 to Advisory Action mailed May 16, 2007 and Final Office Action mailed Jan. 31, 2007", 5 pgs.

"U.S. Appl. No. 10/728,655, Response filed Jun. 6, 2005 to Final Office Action mailed Apr. 5, 2005", 13 pgs.

"U.S. Appl. No. 10/728,655, Response filed Jun. 20, 2006 to Non-Final Office Action mailed Mar. 20, 2006", 12 pgs.

"U.S. Appl. No. 10/728,655, Response filed Nov. 22, 2006 to Non-Final Office Action mailed Aug. 30, 2006", 10 pgs.

"U.S. Appl. No. 10/728,655, Response filed Dec. 21, 2005 to Non-Final Office Action mailed Sep. 21, 2005", 11 pgs.

"U.S. Appl. No. 11/130,723, Response to Restriction Requirement filed Aug. 27, 2009", 6 pgs.

"U.S. Appl. No. 11/277,813, Restriction Requirement mailed Jul. 27, 2009", 6 pgs.

"U.S. Appl. No. 10/758,701, Notice of Allowance mailed May 10, 2006", 3 pgs.

"U.S. Appl. No. 10/758,701, Preliminary Amendment filed Jan. 15, 2004", 5 pgs.

"U.S. Appl. No. 10/758,701, Response filed May 18, 2005 to Restriction Requirement mailed Apr. 19, 2005", 8 pgs.

"U.S. Appl. No. 10/758,701, Restriction Requirement mailed Apr. 19, 2005", 5 pgs.

"U.S. Appl. No. 11/277,813, Non-Final Office Action mailed Aug. 5, 2010", 16 pgs.

"U.S. Appl. No. 12/268,751, Response filed May 12, 2010 to Restriction Requirement mailed Apr. 15, 2010", 6 pgs.

"U.S. Appl. No. 12/268,751, Restriction Requirement mailed Apr. 15, 2010", 8 pgs.

"European Application Serial No. 01992357.2, Response filed Sep. 21, 2009 to Communication mailed Mar. 11, 2009", 23 pgs.

"European Application Serial No. 05776488.8, Office Action mailed Dec. 17, 2009", 6 pgs.

"European Application Serial No. 05776488.8, Office Action Response Filed Jun. 28, 2010", 18 pgs.

"International Application Serial No. PCT/US2001/050257, International Preliminary Examination Report mailed Aug. 8, 2003", 2 pgs.

"Japanese Application Serial No. 2007-518200, Office Action mailed Jun. 29, 2010", 2 pgs.

"U.S. Appl. No. 11/277,813, Response filed Dec. 6, 2010 to Non Final Office Action mailed Aug. 5, 2010", 13 pgs.

"U.S. Appl. No. 12/268,751, Non-Final Office Action mailed Nov. 16, 2010", 7 pgs.

"Japanese Application Serial No. 2007-518200, Office Action Response filed Sep. 29, 2010", 8 pgs.

"U.S. Appl. No. 11/277,813, Response filed May 31, 2011 to Final Office Action mailed Mar. 3, 2011", 9 pgs.

"U.S. Appl. No. 12/268,751, Advisory Action mailed Aug. 3, 2011", 2 pgs.

"U.S. Appl. No. 12/268,751, Response flied Jul. 26, 2011 to Final Office Action mailed May 26, 2011", 6 pgs.

"European Application Serial No. 11158935.4, European Search Report mailed Aug. 11, 2011", 6 pgs.

"U.S. Appl. No. 11/277,813, Final Office Action mailed Mar. 3, 2011", 13 pgs.

"U.S. Appl. No. 12/268,751, Final Office Action mailed May 26, 2011", 7 pgs.

"U.S. Appl. No. 12/268,751, Response filed Mar. 8, 2011 to Non-Final Office Action mailed Nov. 16, 2010", 8 pgs.

"Japanese Application Serial No. 2007-518200, Notice of Allowance mailed Feb. 8, 2011", 1 pg.

"European Application Serial No. 11158935.4, Response filed Mar. 6, 2012 to Extended Search Report mailed Sep. 12, 2011", 107 pgs.

\* cited by examiner

700

```
┌─────────────────────────────┐
│ SETTING THE STAKING MACHINE │─ 710
└─────────────────────────────┘

┌─────────────────────────────┐
│     STACKING THE FOILS      │─ 720
└─────────────────────────────┘

┌─────────────────────────────┐
│   STAKING THE FOILS TOGETHER│─ 730
└─────────────────────────────┘
```

Fig.11

FLAT CAPACITOR HAVING STAKED FOILS AND EDGE-CONNECTED CONNECTION MEMBERS

CROSS-REFERENCE TO RELATED APPLICATIONS

This application is a divisional of U.S. patent application Ser. No. 10/728,655, filed on Dec. 5, 2003, now issued as U.S. Pat. No. 7,347,880, which is a divisional of U.S. patent application Ser. No. 09/706,518, filed on Nov. 3, 2000, now issued as U.S. Pat. No. 6,687,118, the specifications of which are incorporated herein by reference.

This application is related to U.S. Pat. No. 6,699,265, filed on Nov. 3, 2000, entitled FLAT CAPACITOR FOR AN IMPLANTABLE MEDICAL DEVICE, which is incorporated herein by reference in its entirety.

FIELD OF THE INVENTION

The present invention concerns implantable medical devices, such as defibrillators and cardioverters, particularly structures and methods for capacitors in such devices.

BACKGROUND

Since the early 1980s, thousands of patients prone to irregular and sometimes life-threatening heart rhythms have had miniature heart monitors, particularly defibrillators and cardioverters, implanted in their bodies. These devices detect onset of abnormal heart rhythms and automatically apply corrective electrical therapy, specifically one or more bursts of electric current, to hearts. When the bursts of electric current are properly sized and timed, they restore normal heart function without human intervention, sparing patients considerable discomfort and often saving their lives.

The defibrillator or cardioverter includes a set of electrical leads, which extend from a sealed housing into the walls of a heart after implantation. Within the housing are a battery for supplying power, monitoring circuitry for detecting abnormal heart rhythms, and a capacitor for delivering bursts of electric current through the leads to the heart.

The capacitor can take the form of a flat aluminum electrolytic capacitor. Flat capacitors include a stack of flat capacitor elements, with each element including one or more separators between two sheets of aluminum foil. One of the aluminum foils serves as a cathode (negative) foil, and the other serves as an anode (positive) foil. Sometimes, two or more foils are stacked one on the other and connected to form a multi-anode stack. The capacitor elements each have an individual capacitance (or energy-storage capacity) proportional to the surface area of the aluminum foil. Sometimes, each anode foil is etched to increase its surface area and thus to increase the capacitance of its capacitor element.

The anode foils and the cathode foils of the capacitor elements are connected together to provide a total capacitance. A connection member such as an aluminum tab is laid across the surface of an anode or cathode foil and then joined to the foil by a method, such as cold welding or swaging, which results in one or more weld joints. After a connection member has been attached to each anode or cathode foil in the capacitor, the respective connection members are crimped or welded together and attached to feedthrough terminals for connection to circuitry outside the capacitor.

The inventors have identified many problems regarding present connection member-to-foil connections, connection member-to-connection member connections, and foil-to-foil connections that increase the size of the capacitor and decrease its reliability.

For instance, one drawback to present connection member-to-foil joining techniques is that they limit the amount of etching that can be done to the anode foil. This is because etching the anode foil to increase its capacitive surface area makes the foil brittle and prone to cracking under the strain of present welding techniques. To make up for the lost etching, manufacturers need to use additional capacitor elements or larger foils, both of which increase capacitor size. Thus, present connection member-to-foil joining techniques result in larger than desirable capacitors.

Another drawback is that present connection member-to-foil joining techniques require a relatively large weld, and thus a relatively large aluminum connection member (which is governed by the size of the weld). Large connection members can be a problem since placing an aluminum connection member within each anode stack causes a bulge in the anode stack which increase the capacitor volume. Some manufacturers reduce the bulge by cutting a notch into one of the anodes of the stack so that the aluminum connection member fits within the notch and does not bulge the stack. Unfortunately, having a large connection member requires a large notch, which decreases the surface area of the anode and leads manufacturers to increase capacitor size to make up the loss.

One problem with present connection member-to-connection member connections is that they also undesirably increase capacitor size. Presently, each connection member must be long enough to be crimped to the other connection members, and the extra length or slack required to bring them all together increases capacitor size since the capacitor case must be made larger to accommodate the crimped connection members. Moreover, crimping the connection members together stresses the connection member-to-foil connections and it does not result in connection member-to-connection member connection which is electrically reliable. Also, crimping the connection members together results in an irregular surface on which to attach a feedthrough terminal. Thus the performance and reliability of the capacitor suffers.

One drawback with present foil-to-foil connections is that present connection techniques usually limit the amount of etching that can be done to the anode foils since etching the foil makes the foil brittle and prone to cracking under the strain of staking or cold-welding. Moreover, present connection techniques also limit the types and varieties of foils that can be used in a multi-anode stack. For instance, core-etched foils are easier to stake than tunnel-etched foils because of the extra material provided in the solid core.

Another drawback is that anode foils used in implantable medical devices are only able to charge to about 400 volts without breaking down. To reach needed voltage ranges of 600 volts or higher, as used for an implantable defibrillator, for example, two capacitors must be connected in series to deliver the shock pulse. This also increases the overall size of the implantable device.

SUMMARY

To address these and other needs, the inventors devised foil structures, foil-to-foil assembly methods, connection member-to-foil assembly methods, and connection member-to-connection member assembly methods and other connection structures and capacitor structures. In one embodiment, a method includes joining a connection member to a capacitor foil using a staking tool having a tip of less than or equal to approximately 0.030" (0.762 mm) in diameter. A capacitor made using the technique includes an anode having a connection member attached to it by a micro-stake weld joint. Among other advantages, the present connection member-to-foil joining method results in a smaller than typical weld joint which permits increased anode brittleness and smaller foil notches. Thus, with all other capacitor factors being equal, it results in a smaller volume capacitor.

Another aspect couples multiple connection members of a capacitor together by edge-connecting each connection member to its neighboring connection member or connection members so that the connection members need not be crimped together. Another aspect includes a capacitor having one or more anodes having connection members attached to their surfaces. Each connection member has a front surface substantially flush with the front surface of adjacent connection members. Among other advantages, these features provide a capacitor which requires less space for its anode connection members and which has a more reliable connection member-to-connection member connection and reduced stress on the connection member-to-foil connection.

One aspect provides a method of foil-to-foil connecting which includes joining one or more foils using a staking tool having a tip of less than approximately 0.060" (1.524 mm). In other embodiments, the tip ranges from approximately 0.015" (0.381 mm) to approximately 0.060" (1.524 mm). In one embodiment, the tip is approximately equal to 0.025" (0.635 mm) in diameter. Among other advantages, the exemplary foil-to-foil joining method permits increased anode brittleness and allows for different permutations of anode foils.

One aspect provides a capacitor which includes a capacitor case having an electrolyte therein and a high formation voltage anode foil having a porous structure and located within the capacitor case. Among other advantages, the exemplary capacitor provides the high voltages needed for applications such as defibrillation, while the porous foil structure provides for a more space efficient structure.

Another aspect of the present invention includes various implantable medical devices, such as pacemakers, defibrillators, and cardioverters, incorporating one or more capacitors having one or more of the novel features described above.

BRIEF DESCRIPTION OF THE DRAWINGS

FIG. 11 is a flowchart of a method for performing foil-to-foil staking according to one embodiment of the present invention.

DETAILED DESCRIPTION

The following detailed description, which references and incorporates the figures, describes and illustrates one or more specific embodiments of the invention. These embodiments, offered not to limit but only to exemplify and teach the invention, are shown and described in sufficient detail to enable those skilled in the art to practice the invention. Thus, where appropriate to avoid obscuring the invention, the description may omit certain information known to those of skill in the art.

Figure 1:
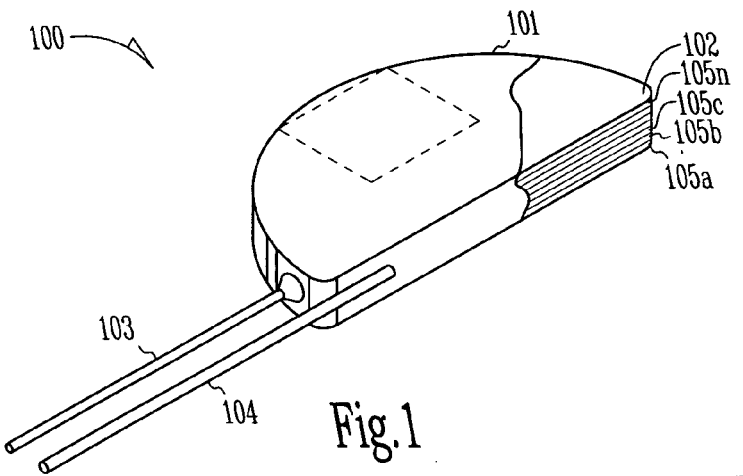
FIG. 1 is an isometric view of a flat capacitor according to one embodiment of the present invention.

FIG. 1 shows a flat capacitor 100 according to one embodiment of the present invention. Although capacitor 100 is a D-shaped capacitor, in other embodiments, the capacitor is any desirable shape, including, but not limited to rectangular, circular, oval, square, or other symmetrical or asymmetrical shape. Capacitor 100 includes a case 101 which contains a capacitor stack 102. In one embodiment, case 101 is manufactured from a conductive material, such as aluminum. In other embodiments, the case is manufactured using a nonconductive material, such as a ceramic or a plastic.

Capacitor 100 includes a first terminal 103 and a second terminal 104 for connecting capacitor stack 102 to an outside electrical component, such as implantable medical device circuitry. In one embodiment, terminal 103 is a feedthrough terminal insulated from case 101, while terminal 104 is directly connected to case 101. Alternatively, the capacitor incorporates other connection methods. For instance, in some embodiments, capacitor 100 includes two feedthrough terminals.

In the present embodiment, capacitor stack 102 includes capacitor modules or elements 105a, 105b, 105c, . . . , 105n.

Figure 2:
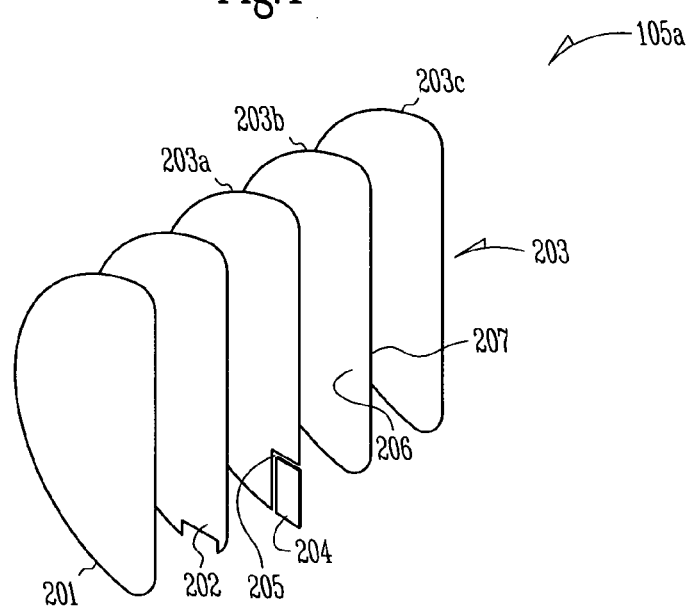
FIG. 2 is an exploded isometric view of portions of the capacitor of FIG. 1.

FIG. 2 shows details of one example of capacitor element 105a, which is representative of capacitor elements 105b-105n. Element 105a includes a cathode 201, a separator 202, and an anode stack 203. In other embodiments, other numbers and arrangements of anodes, cathodes, and separators are utilized.

Cathode 201 is a foil attached to other cathodes of capacitor stack 102 and to terminal 104. In some embodiments, cathode 201 can include aluminum, tantalum, hafnium, niobium, titanium, zirconium, and combinations of these metals. In one embodiment, cathode 201 is constructed by taking an aluminum (98% purity or higher) base metal and coating it with titanium oxide, titanium nitride, or titanium pentoxide using sputtering, plating, vacuum deposition, or other coating techniques. In some embodiments, titanium itself is used with a subsequent processing step used to oxidize the titanium resulting in TiO, $TiO_2$, TiN, $Al_2O_5$, or other high dielectric constant oxide.

The resulting titanium-coated cathode material has a higher capacitance per unit area than traditional aluminum electrolytic capacitor cathodes. Traditional cathodes which are 98% aluminum purity or higher generally have capacitance per unit area of approximately 250 $uF/cm^2$ for 30 micron thick foil, with an oxide breakdown voltage in the 1-3 volt range. However, a cathode as described above results in a capacitance per unit area which, in some embodiments, is as high as 1000 $uF/cm^2$ or more.

Advantageously, this provides a single cathode which services several layers of anodic foil without exceeding the oxide breakdown voltage. When using a traditional cathode to service several layers (2 or more) of anodic foil, the cathode voltage may rise as high as 5 or more volts, which is usually greater than the breakdown voltage. When this occurs, the aluminum cathode begins to form oxide by a hydration process which extracts oxygen from the water present in the electrolyte. The reaction produces hydrogen as a byproduct which in turn has the effect of creating an internal pressure within the capacitor causing an undesirable mechanical bulge. Therefore, the titanium-coated cathode described above serves as a corrective mechanism to hydrogen generation.

Separator 202 is located between each anode stack 203 and cathode 201. In one embodiment, separator 202 consists of two sheets of kraft paper impregnated with an electrolyte. In some embodiments, separator 202 includes a single sheet or three or more sheets.

The electrolyte can be any suitable electrolyte for an electrolytic capacitor, such as an ethylene-glycol base combined with polyphosphates, ammonium pentaborate, and/or an adipic acid solute. In one embodiment, the electrolyte includes butyrolactone and ethylene glycol, such as B103AD electrolyte manufactured by Boundary Technologies, Inc. of Northbrook, Ill. 60065 USA. In one embodiment, the electrolyte is an electrolyte such as is described in U.S. Pat. No. 5,507,966 to Liu entitled ELECTROLYTE FOR AN ELECTROLYTIC CAPACITOR.

In one embodiment, each anode stack 203 is a multi-anode stack including three anode foils 203a, 203b, and 203c. In other embodiments, anode stack 203 includes one, two, three or more anode foils having a variety of anode shapes. Each anode foil has a major surface 206 and an edge face 207 generally perpendicular to major surface 206. Anodes 203a, 203b, and 203c are generally foil structures and can include aluminum, tantalum, hafnium, niobium, titanium, zirconium, and combinations of these metals.

In one embodiment, anode foils 203a-203c are high formation voltage anode foils, which will be discussed below. In other embodiments, the anode foils are medium and/or low formation voltage foils. In one embodiment, the major surface of each anode foil 203a-203c is roughened or etched to increase its microscopic surface area. This increases the microscopic surface area of the foil with no increase in volume. Other embodiments use tunnel-etched, core-etched, and/or perforated-core-etched foil structures, such as those shown in U.S. patent application Ser. No. 09/165,779 entitled HIGH-ENERGY CAPACITORS FOR IMPLANTABLE DEFIBRILLATORS, which is incorporated herein by reference in its entirety. Other embodiments utilize other foil compositions and classes of foil compositions.

Attachable to anode stack 203 at major surface 206 of anode 203b is a foil connection structure such as a tab or connection member 204, made from aluminum, which electrically connects each anode foil to the other anodes of the capacitor. For instance, in the present embodiment, each tab or connection member 204 of each capacitor element 105a, ..., 105n is connected to each other connection member 204 and coupled to terminal 103 for electrically coupling the anode to a component or electronic assembly outside the case. In one embodiment, each anode 203a includes a notch 205 which is slightly larger than the width of connection member 204. Connection member 204 fits within notch 205, and this prevents connection member 204 from causing a bulge in anode stack 203. However, other embodiments omit the notch to avoid reducing the surface area of anode 203a. In other embodiments, connection member 204 is omitted and an integrally connected tab connection member is utilized for one or more anode foils.

Figure 3:
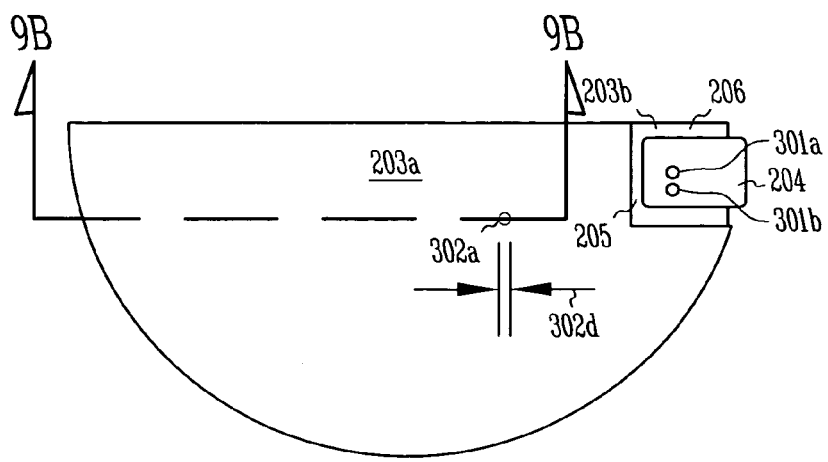
FIG. 3 is a top view of a connection member-to-foil connection and a foil-to-foil connection according to one or more embodiments of the present invention.

FIG. 3 shows a top view of capacitor element 105a. In one embodiment, each anode foil 203a-203c of multi-anode stack 203 is interconnected to the other foils 203a-203c of multi-anode stack 203 at a stake weld joint 302a, which will be discussed in more detail below.

In one embodiment, connection member 204 is attached to major surface 206 of anode 203b. Member 204 is attached to anode 203b by a method the inventors call micro-staking. Micro-staking is a cold welding or staking process which uses a small staking point. In one embodiment, each micro-stake joint 301a and 301b is approximately 0.015" (0.381 mm) in diameter. In other embodiments, micro-stake joints 301a and 301b are less than or equal to approximately 0.030" (0.762 mm) in diameter. In some embodiments, joints 301a and 301b can range from approximately 0.005" (0.127 mm) to approximately 0.030" (0.762 mm). In some embodiments, joints 301a and 301b can range from approximately 0.010" (0.254 mm) to approximately 0.020" (0.508 mm).

The small size of joints 301a and 301b allows one to use smaller connection members 204 and to place them closer to an edge 303 of anode 203b than typical capacitors. For instance, in one embodiment, joints 301a and 301b are approximately 0.120" (3.048 mm) from edge 303, and joint 301a is approximately 0.100" (2.54 mm) away from the top edge of foil 206. This in turn allows notch 205 to be smaller than in typical capacitors. For instance, in one embodiment, notch 205 is approximately 0.200" by 0.200" (5.08 mm by 5.08 mm). A smaller notch allows more surface area for anode 203a and thus more capacitance per unit volume. The small size of joints 301a and 301b also allows use of a more highly etched, and hence more brittle, foil since making the small weld joint is less likely to crack the brittle foil than large weld joints.

In one embodiment, member 204 is attached to anode 203b at two micro-stake joints, 301a and 301b. Some embodiments only have a single micro-stake joint 301 and others have three or more micro-stake joints. However, the two welds of this embodiment allow for a redundant weld in case either of the welds fail. In other embodiments, tab 204 is attached by other techniques, such as laser welding or soldering. In one embodiment, tab 204 is attached only to a single anode foil, anode 203b.

Figure 4:
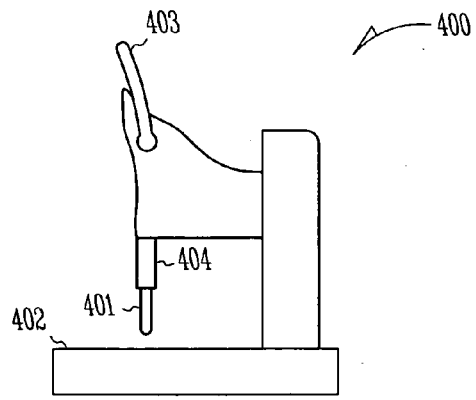
FIG. 4 is a side view of a staking machine having a staking tool for performing staking according to one embodiment of the present invention.

FIG. 4 shows a staking machine 400 for making micro-stake joints 301a and 301b according to one embodiment. Machine 400 includes a hardened, planar, anvil surface 402 and a handle 403. A micro-staking tool 401 is shown installed in machine 400. In one embodiment, machine 400 is a hand-operated press manufactured by Gechter Co. of Germany. Alternatively, by way of example, but not limitation, other cold-welding machines, pneumatic presses, electronic solenoid, electro-punch, air over hydraulic, or hydraulic presses can be used to perform the micro-staking process.

Tool 401 is held within a tool holder or collet 404 which is operatively coupled to handle 403. Pulling handle 403 moves collet 404 and tool 401 towards surface 402. Alternatively, as noted above, pneumatic pressure, an electric driver, hydraulic, solenoid, or other actuation means can be used to activate tool 401.

Figure 5:
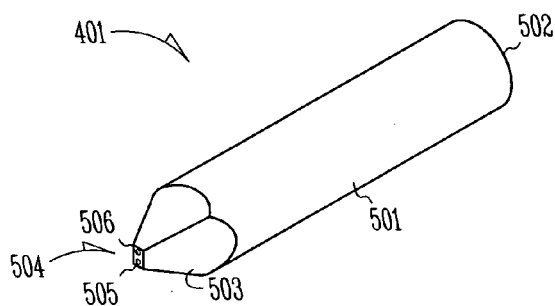
FIG. 5 is an isometric view of the staking tool of FIG. 4.
Figure 6:
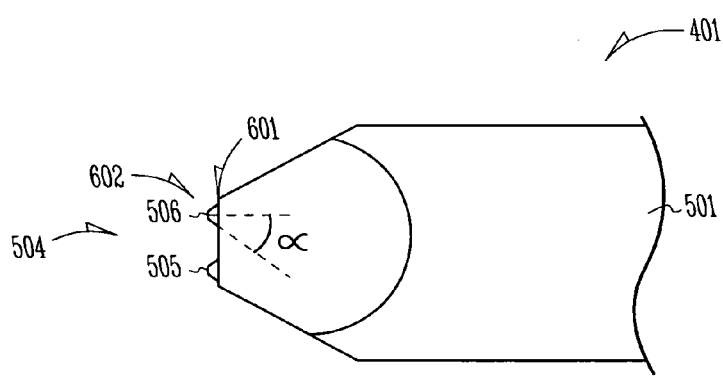
FIG. 6 is a enlarged side view of the staking tool of FIG. 5.

FIGS. 5 and 6 show details of micro-staking tool 401 for performing connection member-to-foil staking according to one embodiment of the present invention. Tool 401 is machined from a stainless steel or a tool steel. Tool 401 includes a first end 502 for mounting to collet 404 and a second end 504 for making the micro-staked joints. End 504 includes a first staking pin 505 and a second staking pin 506. In one embodiment, pins 505 and 506 are approximately 0.040" (1.016 mm) apart. In some embodiments, a single pin 505 is used for making a single weld joint.

In one embodiment, each pin 505 and 506 has a generally frusto-conical shape rising at an angle α of approximately 30°. Each pin has a circular cross-section having a diameter of approximately 0.028" (0.7112 mm) at its base 601 and a diameter of approximately 0.015" (0.381 mm) at its tip 602. Alternatively, tip 602 can range in diameter from approximately 0.005" (0.127 mm) to approximately 0.030" (0.762 mm); some embodiments range from approximately 0.010" (0.254 mm) to approximately 0.030" (0.762 mm); other embodiments range from equal to or greater than approximately 0.030" (0.762 mm) in diameter. In other embodiments, tip 602 is less than or equal to approximately 0.030" (0.762 mm) in diameter. In some embodiments, tip 602 ranges from approximately 0.010" (0.254 mm) to approximately 0.020" (0.508 mm). By way of example, the pin can have an oval, diamond, elliptical, rectangular, square, or other shaped cross-section. In one embodiment, the tip of each pin 505 and 506 is flat. However, in other embodiments, the tips are domed, concave, convex, rounded, or indented and may include a plurality of angles.

Figure 7:
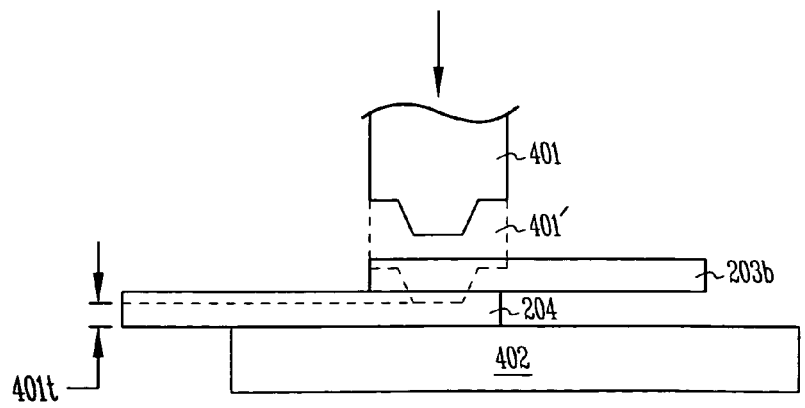
FIG. 7 is an enlarged side view of the staking machine of FIG. 4.

FIG. 7 shows a close-up view of one embodiment of tool 401 being used to micro-stake connection member 204 to anode 203b. In one embodiment, connection member 204 rests against hardened surface 402 and anode 203b lies between connection member 204 and tool 401. Such an arrangement (wherein the connection member rests against the hardened surface and the anode foil is above it) of connection members and foils decreases the likelihood of cracking the brittle foil of anode 203b during micro-staking.

In one embodiment, the hand-operated staking machine is set so that there is a distance 401t of approximately 0.001" (0.0254 mm) between anvil surface 402 and tool 401 when the tool is in its lowest or terminal position 401'. To micro-stake connection member 204 to anode 203b, tool 401 is driven first into anode 203b, which is compressed into connection member 204. In one embodiment, tool 401 is driven to a displacement of 0.001" (0.0254 mm) when micro-staking. In other embodiments, where air, hydraulic, or solenoid force is used, tool 401 is driven under a force in the range of 100 to 1000 pounds until the tool bottoms out. In those embodiments, there is no set clearance.

Figure 8:
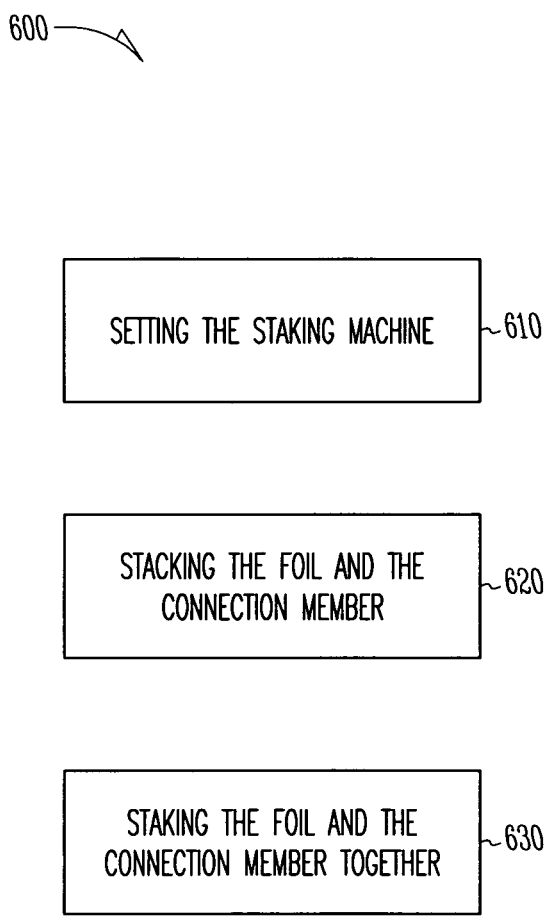
FIG. 8 is a flowchart depicting a method for performing connection member-to-foil staking according to one embodiment of the present invention.

FIG. 8 shows a flowchart of one example of a method 600 of joining a connection member and a foil together. Method 600 includes process blocks 610-630. Block 610 entails setting a staking tool; block 620 entails stacking the connection member and the foil; and block 630 entails forcing the foil and connection member together. In one embodiment, a staking machine such as machine 400 having hardened surface 402, and a staking tool such as tool 401 having at least one staking pin 505, are used to perform the method.

Block 610 includes setting staking pin 505 so that there is an approximately 0.001" (0.0254 mm) clearance or displacement between anvil surface 402 and pin 505 when the tool is in its lowest or terminal position. Typically this is done when machine 400 is a hand-operated press.

In some embodiments, block 610 is omitted. For instance, as noted above, pneumatic, hydraulic, air over hydraulic, electric solenoid, electric driver, or other actuation means can be used to activate tool 401. In these embodiments, tool 401 is set to be driven under a force of approximately 100 pounds to 1000 pounds until it bottoms out or until a pre-determined displacement is reached.

Block 620 includes placing a connection member, for instance connection member 204, on hardened surface 402 and stacking or placing a foil, such as foil 203b, on top of connection member 204.

In block 630, the staking machine is activated so that tool 401 drives downward and forces the foil and the connection member together between hardened surface 402 and staking pin 505.

The micro-staking process results in the micro-staked weld joints 301a and 301b as shown in FIG. 3. As described above, in one embodiment, these welds are relatively close to edge 303 of the anode. Thus, a relatively small connection member can be used and a relatively small notch can be used in the notched anode, such as anode 203a. This increases the capacitive surface area of the anode without increasing the volume of the capacitor itself, thus increasing its energy density.

Referring again to FIG. 3, each anode foil 203a-203c of multi-anode stack 203 is interconnected to the other foils 203a-203c of multi-anode stack 203 at a stake weld joint 302a. In one embodiment, foil-to-foil joint 302a has a diameter 302d of approximately 0.025" (0.635 mm). In some embodiments, joint diameter 302d is less than approximately 0.060" (1.524 mm). In various embodiments, joint diameter 302d ranges from approximately 0.015" (0.381 mm) to less than approximately 0.060" (1.524 mm).

Figure 9A:
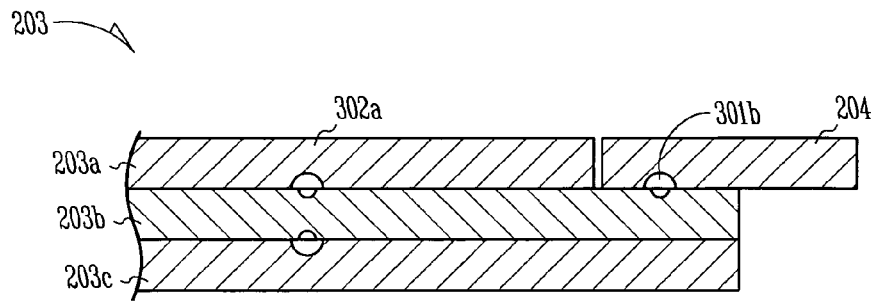
FIG. 9A is a cross-sectional side view of portions of the capacitor stack of FIG. 3.

FIG. 9A shows a cross-sectional view of the foil connection of anode stack 203. Foils 203a-203c are connected by foil-to-foil weld 302a and tab 204 is attached to anode 203b by weld 301b. In various embodiments, foils 203a-203c are different types of etched foils. For example, in one embodiment, all three foils 203a-203c are tunnel-etched foils. In another embodiment, at least one of the foils, for example, foil 203b is a core-etched foil or a perforated core-etched foil. Other embodiments present other permutations of foils. The present joining method is able to successfully join various permutation of materials, thus permitting capacitor manufacturers to design the capacitor with fewer material limitations.

Figure 9B:
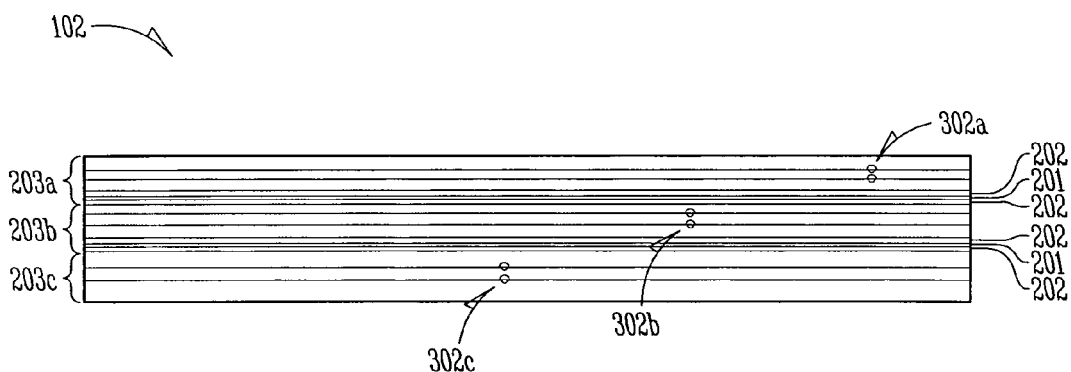
FIG. 9B is a cross-sectional side view of portions of the capacitor stack of FIG. 3.

FIG. 9B shows a cross-sectional view of portions of capacitor stack 102. In the portion shown, capacitor stack 102 includes anode stacks 203a-203c. Between each anode stack is separator 202 and cathode 201. Each anode stack is joined by respective stake welds 302a-302c. In the exemplary capacitor stack, each stake weld 302a-302c of each anode stack 203a-203c is in a different location relative to the major surface of each anode stack. This staggered arrangement of welds provides that the bulges created at any single weld 302a-302c do not cumulate along any single point or vertical line in the capacitor stack. This staggered arrangement helps reduce the overall thickness of capacitor stack 102.

Figure 10:
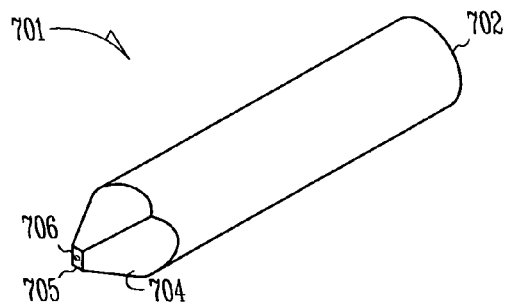
FIG. 10 is an isometric view of a staking tool for performing foil-to-foil staking according to one embodiment of the present invention.

FIG. 10 shows a staking tool 701 for staking foils 203a-203c together according to one embodiment of the present invention. In one embodiment, a staking machine such as described in FIG. 4 is used. Alternatively, other cold welding machines, pneumatic presses, hydraulic, air over hydraulic, or electric solenoid machines are used to perform the staking process.

In some embodiments, such as when the staking machine is hand-operated, tool 701 is driven to a displacement of 0.001" (0.0254 mm) from the hardened surface of the staking machine when the staking is being done. In some embodiments, such as when pneumatic, hydraulic, air over hydraulic, or electric solenoid presses are used, tool 701 is driven under a force of approximately 100 pounds to 1000 pounds until it bottoms out or until a pre-determined displacement is reached.

In one embodiment, tool 701 is machined from a stainless steel or a tool steel. Tool 701 includes a first end 702 for mounting to a collet in a staking machine and a second end 704 for making the foil-to-foil staked joints. End 704 includes a stake pin 705 having a tip 706.

In one embodiment, pin 705 has a generally frusto-conical shape rising at an angle α of approximately 30°. The exemplary pin has a circular cross-section. Pin 705 can also have an oval, diamond, elliptical, rectangular, or square shaped cross-section. Pin 705 has a diameter of approximately 0.025" (0.635 mm) at tip 706. Alternatively, in some embodiments, tip 706 is less than approximately 0.060" (1.524 mm). In various embodiments, tip 706 ranges from approximately 0.015" (0.381 mm) to less than approximately 0.060" (1.524 mm). In one embodiment, the tip of pin 705 has a flat surface. However, in other embodiments, the tip is domed, convex, concave, rounded, or may have a plurality of angles.

FIG. 11 shows a flowchart of one example of a method 700 of assembling two or more anode foils, such as anodes 203a-203c. In one method, three anodes are joined. In other embodiments two, three, four, or more foils are joined using the method. In some embodiments, method 700 joins a stack of foils which includes one or more core-etched foils. However, in various other embodiments, method 700 joins a stack comprising only tunnel-etched foils.

Method 700 includes process blocks 710-730. Block 710 entails setting a staking tool; block 720 entails stacking foils; and block 730 entails forcing the foils together. In one embodiment, a staking machine such as machine 400 having hardened surface 402, and a staking tool such as tool 701 having staking pin 705 are used to perform the method.

Block 710 includes setting staking pin 705 so that there is an approximately 0.001" (0.0254 mm) clearance or displacement between hardened surface 402 and pin 705 when the tool is in its lowest or terminal position. Typically this is done when the staking machine is a hand-operated press.

In some embodiments, block 710 is omitted. For instance, as noted above, pneumatic, hydraulic, air over hydraulic, electric solenoid, electric driver, or other actuation means can be used to activate tool 701. In these embodiments, tool 701 is set to be driven under a force of approximately 100 pounds to 1000 pounds until it bottoms out or until a pre-determined displacement is reached.

Block 720 includes placing a first foil, for instance foil 203c, on hardened surface 402 and stacking or placing one or more foils, such as foils 203b and 203a, on top of foil 203c so that the major surfaces of adjacent foils are in contact with each other and the foils are stacked in a dimension perpendicular to a major surface of each of the foils. After block 720, foil stack 203 is positioned between hardened surface 402 and staking tool 701. In some embodiments, two, three, four or more foils are stacked on the hardened surface.

In block 730, the staking machine is activated so that tool 701 drives downward and forces the anode foils between hardened surface 402 and staking pin 705. In one method, the tool is driven until a displacement of 0.001" (0.0254 mm) between hardened surface 402 and pin 705 is reached. Alternatively, as noted above, if pneumatic, hydraulic, air over hydraulic, electric solenoid, electric driver, or other actuation means are used to activate tool 701, the tool is set to be driven under a force of approximately 100 pounds to 1000 pounds until it bottoms out or until a pre-determined displacement is reached. One embodiment of staking method 700 results in the weld joint 302a as shown in FIG. 3.

Among other advantages of the present method, since joint 302a is small, a more brittle foil can be used and this increases the capacitive surface area of the anode without increasing the volume of the capacitor itself, thus increasing its energy density. Also, a wide variety of foil types can be staked together.

In one embodiment, tab or connection member 204 is staked or micro-staked to anode 203b before the foils 203a-203c are staked together by method 700. Attaching the connection member to only one foil decreases the chance of the highly etched and brittle foil cracking under the stress of the weld. This allows use of foils with greater degrees of etching and thus, smaller volume capacitors.

In assembling capacitor 100, one example method includes assembling two or more anode stacks 203 by method 700. In one embodiment, each anode stack of capacitor 100 has a respective weld 302a-302c in a different location relative to the major surface of the anode stacks. The two or more anode stacks are assembled into capacitor elements 105a-105n. Each anode tab 204 of each element 105a-105n is connected to each adjacent anode tab 204. In one embodiment, the connection members 204 are connected to each other by a method called edge-welding. In other embodiments, the tabs are connected by staking, laser welding, ultrasonic welding, or other methods.

Figure 12:
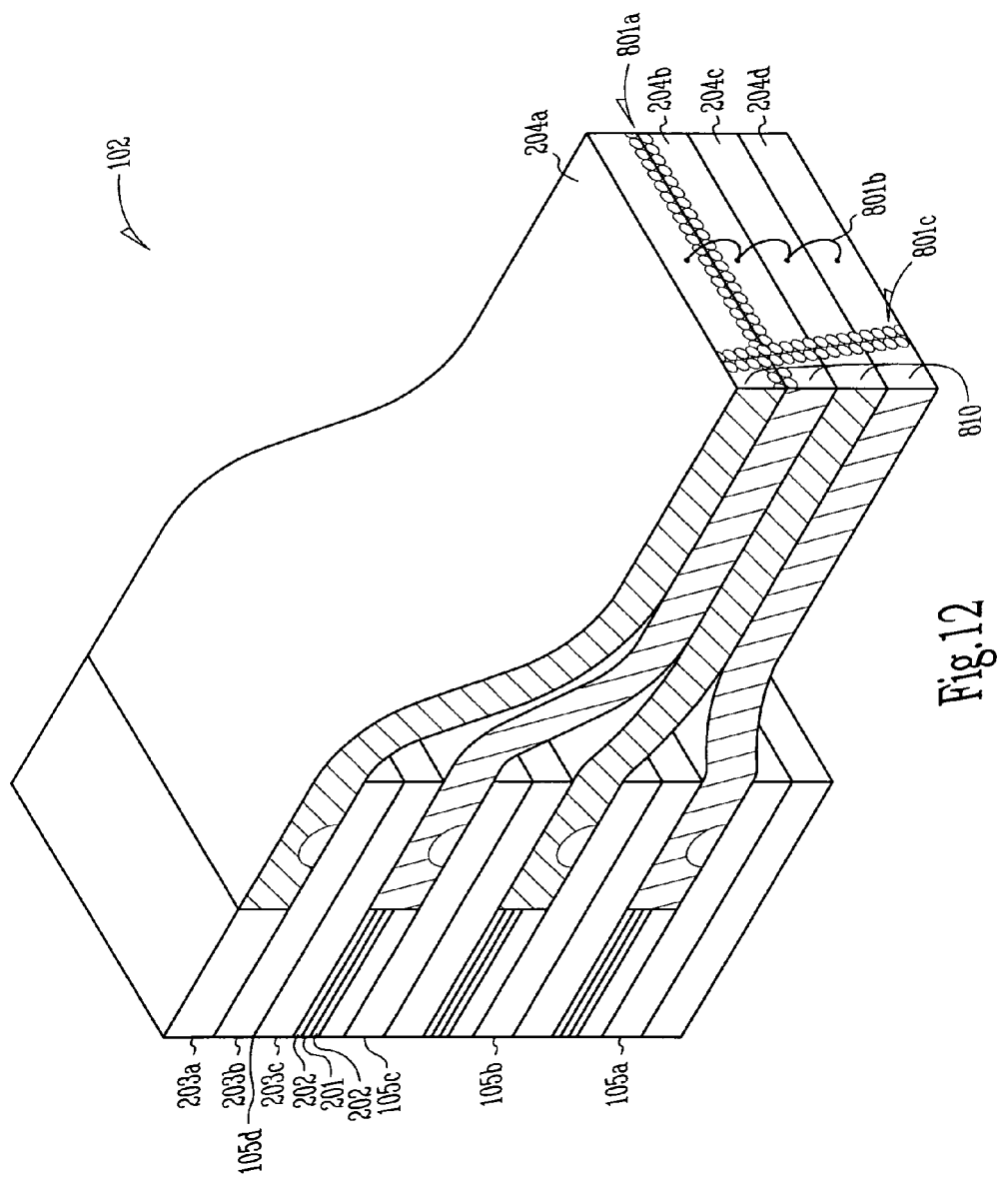
FIG. 12 is a cross-sectional isometric view of a capacitor having edge-connected connection members according to one embodiment of the present invention.

FIG. 12 shows a connection member-to-connection member connection according to one embodiment of the present invention. In the partial view shown, each capacitor element 105a-105d has a respective tab or connection member 204a-204d attached to it by an attachment method. In one embodiment, micro-staking is used to connect the connection members. In one embodiment, each connection member 204a-204d is approximately 0.004" (0.1016 mm) thick to fill the notch of anode foil 203a, which is 0.004" (0.1016 mm) thick. In other embodiments, the anode foil and the cathode and paper assembly have different thicknesses and so does the connection member. In some embodiments, anode 203a is not notched and each connection member 204a-204d is sandwiched between a pair of foils.

Each connection member 204a-204d is positioned so that an exposed front end face 810 of each connection member is flush with the exposed front end faces of its neighboring connection members, forming a flat frontal surface area. In some embodiments, the end faces 810 are cut to be flush with each other. The exposed face or surface of each connection member is the surface or face of the connection member that is open or revealed on the outside of capacitor stack 102.

Each connection member 204a-204d is connected to its neighboring connection members along their respective front faces 810. Three different embodiments of edge connections 801 are shown. Connections 801 include a laser seam edge-weld 801a, a wire bonded connection 801b, and a laser cross-wise edge-weld 801c. However, in the present embodiment only one need be used at any given time. In one embodiment (not shown), edge connection 801 is provided by an ultrasonic edge weld.

In one embodiment, laser edge-weld 801a is provided by a Lumonics JK702 Nd-YAG laser welder using settings of approximately 1.4 Joules at a frequency of 100 hertz. The laser power is approximately 110 Watts, the pulse height is approximately 22%, and the pulse width is approximately 1.4 msec. In various embodiments, the pulse width ranges from about 1.0 ms to about 2.5 ms and the energy level ranges from about 0.8 J to about 2.0 J. In the present process, the connection members are held together in a vice, and the laser beam diameter is approximately 0.011" (0.279 mm). The laser beam is applied along the edge of connection members 204a-204d in a longitudinal manner incrementing to the left or to the right. Alternatively, other welding patterns are used to edge-weld connection members 204a-204d. In some embodiments, the connection members are welded along the horizontal axis, perpendicular to the edges of the connection members 204a-204d. (As shown in cross-wise edge-weld 801c).

Edge-connecting connection members 204a, 204b, 204c, and 204d to each other provides a better electrical connection than crimping them together. Moreover, edge-connection 801 creates a substantially flat, front surface area on the end of the connection members for attachment of a feedthrough terminal or a ribbon connection member (not shown).

Figure 13:
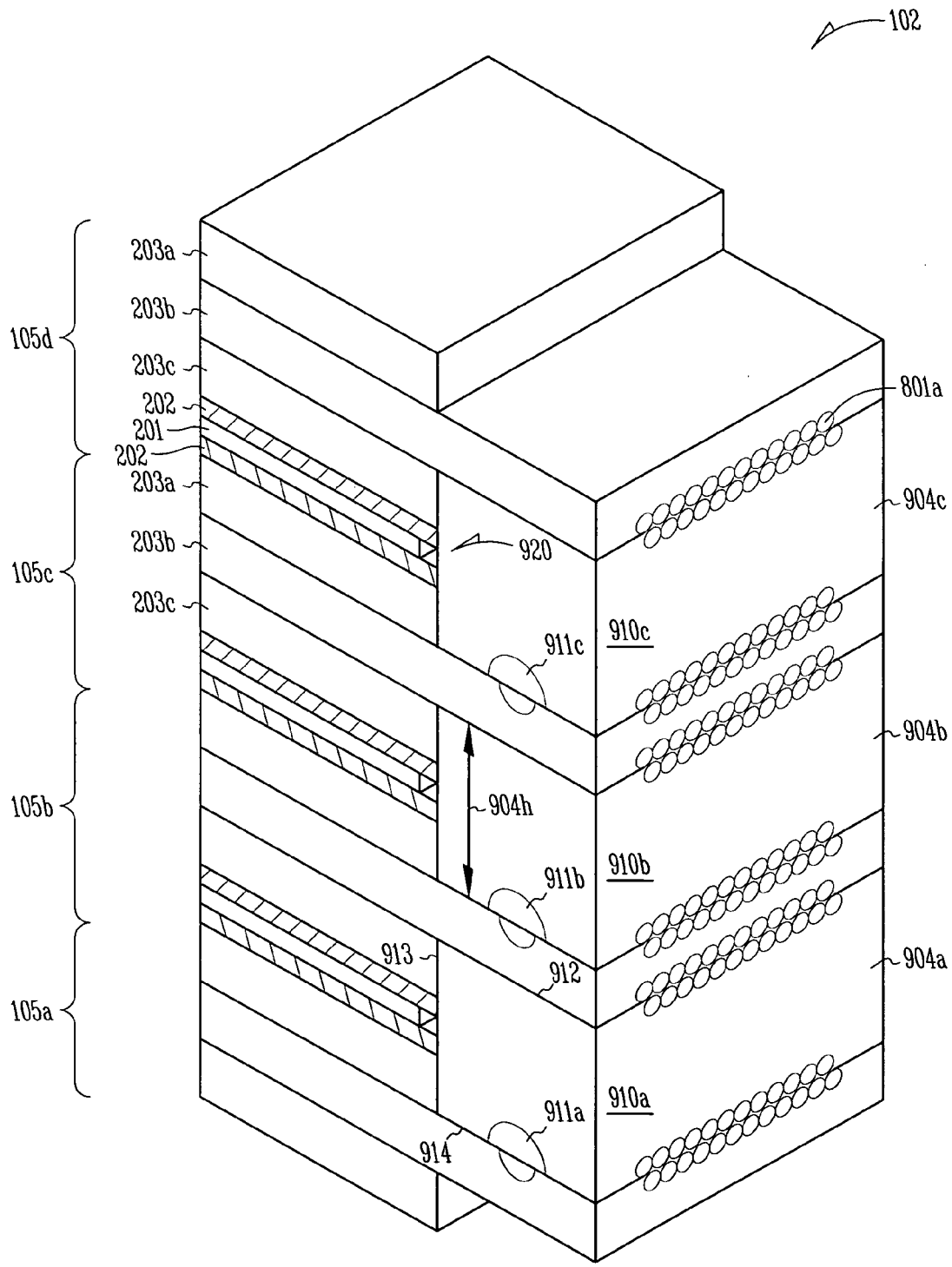
FIG. 13 is a cross-sectional isometric view of a capacitor having edge-connected connection members according to another embodiment of the present invention.
Figure 14:
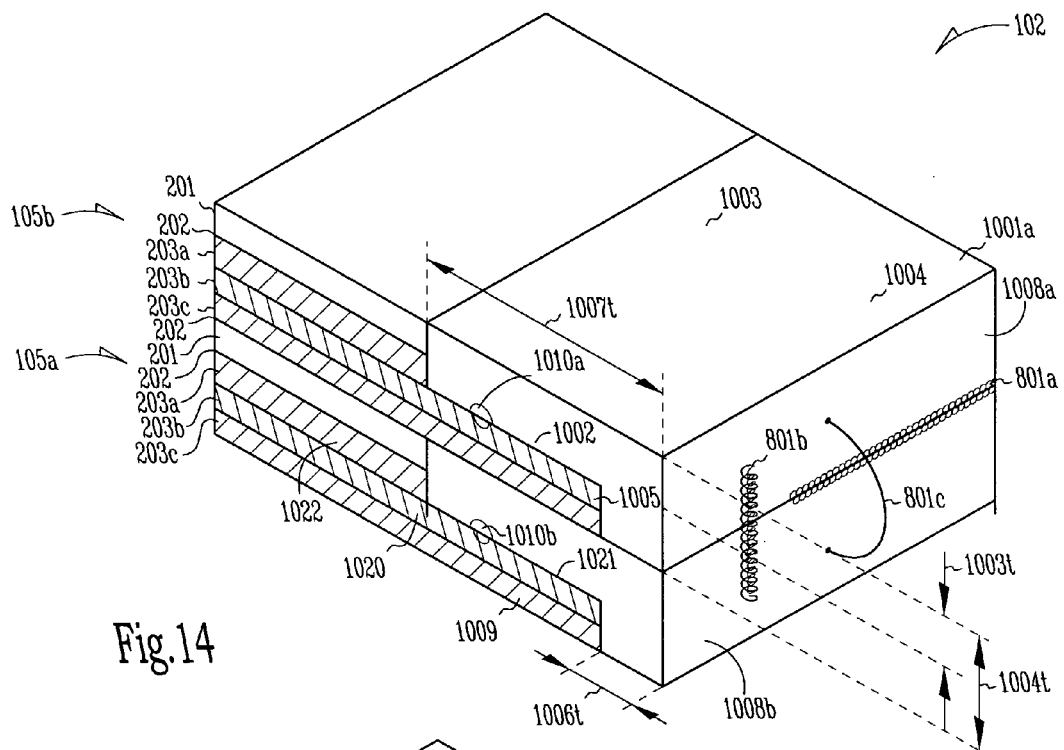
FIG. 14 is a cross-sectional isometric view of a capacitor having edge-connected connection members according to another embodiment of the present invention.
Figure 15:
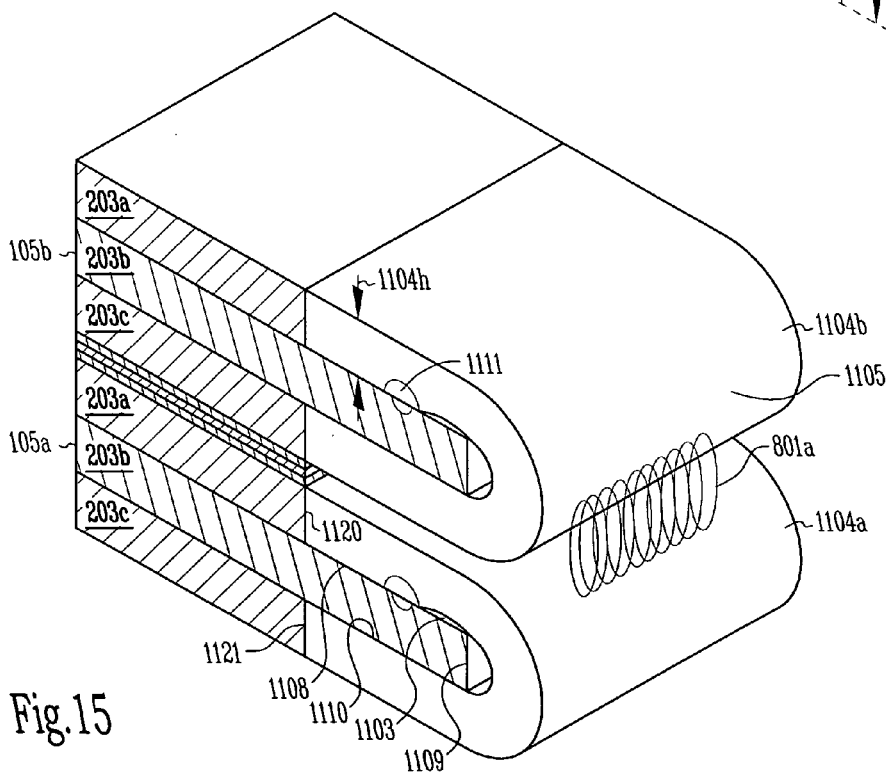
FIG. 15 is a cross-sectional isometric view of a capacitor having edge-connected connection members according to another embodiment of the present invention.

FIGS. 13-15 show other embodiments of various connection member structures and anode layouts that are used for edge-connecting as shown in FIG. 12. In each embodiment shown, anode foils 203a-203c each have a thickness of 0.004" (0.1016 mm) and each cathode 202 and paper separator 201 layer has a combined thickness of 0.002" (0.0508 mm). These thicknesses are exemplary and for the purpose of describing the various exemplary connection member structures. In some embodiments, the various structures and features of FIGS. 12-15 are combined with each other.

FIG. 13 shows one embodiment in which each capacitor element 105 includes two notched anodes, anode 203a on the top of the stack and anode 203c on the bottom of the stack and an un-notched middle anode 203b. Some embodiments include two or more top, bottom, and middle anodes. When two or more elements (such as elements 105c and 105d) are stacked, the notch of top anode 203a of lower element 105c and the notch of bottom anode 203c of upper element 105d define a major notch 920. Each major notch, such as major notch 920, receives connection members 904a, 904b, and 904c so that the connection members do not cause a bulge in the anode stack. Each capacitor element 105a-105c has respective connection member 904a-904c attached to it by micro-staking or other attachment method at respective joints 911a-911c.

In this embodiment, each connection member 904a-904c is block-shaped and has a height 904h of approximately 0.014" (0.3556 mm). This allows each connection member to fill the space created by the 0.004" (0.1016 mm) anodes and the 0.0012" (0.0305 mm) cathode 201, and by separators 202. In other embodiments, different thicknesses of anodes, cathodes, paper, and connection members are used.

In one embodiment, each connection member 904a-904c includes four faces 910, 912, 913, and 914. In one embodiment, adjacent faces (such as 912 and 913) are perpendicular to each other. In some embodiments, other angles and shapes are used. Back face 913 abuts or confronts the edge face of top anode 203a of lower capacitor element 105c and the edge face of bottom anode 203c of upper element 105d. Top and bottom faces 912 and 914 abut the major surfaces of adjacent middle anodes 203b.

Each connection member 904a-904c is positioned and sized to fit within the notches of anodes 203a and 203c so that there is no overhang of the connection member over the edge of the anodes (in one embodiment, each connection member is 0.050" (1.27 mm) deep) and so that the exposed front face 910 of each connection member is substantially flush and evenly aligned and substantially co-planar with its neighboring connection members and with the edge of anode 203b, forming a flat frontal surface area. This flat surface provides an excellent surface for performing laser edge-welding or other edge-connecting.

Each connection member 904a-904c is edge-connected to its neighboring connection members at their respective exposed front faces 910a-910c. Since there is no need to squeeze connection members 904a-904c together before they are edge-connected, less stress is put on the connections 911a-911c.

FIG. 14 shows one embodiment in which each capacitor element 105 includes one notched anode 203a for receiving connection members 1001a and 1001b without causing a bulge in anode stack 203. Each capacitor element 105a and 105b has respective connection member 1001a and 1001b attached to it by micro-staking or other attaching method at a weld joint 1010.

In this embodiment, each connection member 1001a and 1001b is a bracket-shaped member and includes a cut-out section 1002, which gives connection members 1001a and 1001b a stepped-shaped or L-shaped body having two surfaces at right angles to each other. The L-shaped body includes a first section 1003 and a second, thicker section 1004. First section 1003 provides a generally planar surface 1020 for attaching to a major surface 1021 of anode 203b, while an upper face of section 1003 abuts the lower major surface of anode 203c. Section 1003 includes a back face 1022 which abuts the edge face of anode 203a. In one embodiment, first section 1003 has a thickness 1003t of approximately 0.004" (0.1016 mm), which is approximately the same thickness as anode 203a. Section 1003 has a length 1007t of approximately 0.050" (1.27 mm).

Second section 1004 provides a surface substantially perpendicular to surface 1020 of section 1003. The inner surface or face 1009 of section 1004 overhangs and confronts the edge faces of anodes 203b and 203c. An outer face 1008 of section 1004 provides an exposed surface for being edge-connected to its neighboring connection members. In one embodiment, second section 1004 has a thickness 1004t of approximately 0.014" (0.3556 mm), which is approximately the same thickness as the total thickness of anodes 203a, 203b, 203c, cathode 201, and separator 202. This provides that each connection member is flush with and abutting the next connection members in the capacitor and that an excellent aluminum surface is exposed for laser edge-welding and other edge-connecting. In one embodiment, second section 1004 has a width 1006t of about 0.020" (0.508 mm).

In other embodiments, the size of cut-out 1002 and the dimensions of sections 1003 and 1004 of connection members 1001a and 1001b are governed by or proportional to the thickness of the anodes of a capacitor. In general, connection members 1001 are designed to permit second section 1004 to overhang and confront the front edge of anodes 203b and 203c and to lie flush with the next adjacent connection member in the capacitor. For example, in one embodiment (not shown), both anodes 203a and 203b are notched and connection member first section 1003 has a thickness of approximately 0.010" (0.254 mm) (thus filling the 0.010" notch) while second section 1004 still has a thickness of approximately 0.014" (0.3556 mm). In other embodiments, different sized anodes, cathodes, paper, and connection members are used.

Each connection member 1001*a* and 1001*b* is edge-connected to its neighboring connection members. Since there is no need to squeeze connection members 1001*a* and 1001*b* together before they are edge-connected, there is less stress on the connections 1010*a* and 1010*b*. Furthermore, each connection member takes up less overall space, thus saving space within the capacitor.

In some embodiments, the connection members have a T-shape cross-section or other shapes which provide a first section for attaching to the anode foil and a second section for confronting the front edge of the foil.

FIG. 15 shows one embodiment in which each capacitor element 105 includes two notched anodes, anode 203*a* on the top of the stack and anode 203*c* on the bottom of the stack, and one or more anodes 203*b* not having notches. Each capacitor element 105*a*-105*b* has a respective connection member or connection member 1104*a*-1104*b* attached to it by microstaking or other attaching method at respective weld joints 1111*a*-1111*b*. In one embodiment, each connection member 1104*a*-1104*b* has a height 1104*h* of approximately 0.004" (0.1016 mm) to approximately match the thickness of the anode foil. This leaves a small gap in the notch between the connection members. In one embodiment, each connection member has a thickness of about 0.005" (0.127 mm) so that the notch is completely filled. In other embodiments, differences in size, anode, cathode, paper, and connection members may be used without departing from the scope of the present invention.

In this embodiment, each connection member 1104*a*-1104*b* is originally a flat strip and is wrapped around anode 203*b* to cover and confront the front edge of the anode foil to create a U-shaped cross-section. Alternatively, in some embodiments, each connection member 1104 is originally manufactured with a U-shaped profile or cross section and is placed into a position as shown.

Each connection member 1104*a*-1104*b* has an inner surface 1103 and an outer surface 1105. Inner surface 1103 includes a first section 1108 abutting a major top surface of middle anode 203*b*, a second section 1110 abutting a major bottom surface of anode 203*b*, and a third section 1109 confronting an edge face of anode 203*b*. Surface section 1109 is substantially perpendicular to sections 1108 and 1110, while sections 1108 and 1109 are substantially parallel to each other. In one embodiment, surface 1110 is attached to anode 203*b*.

Each connection member 1104 fits within the notches of anodes 203*a* and 203*c* so that outside surface 1105 of each connection member is exposed and aligned with its neighboring connection members, thus forming a frontal surface area which is exposed for being edge-connected.

Each connection member 1104 is edge-connected to its neighboring connection members. Since there is no need to squeeze connection members 1104*a*-1104*b* together before they are edge-connected, there is less stress on the connection member-to-anode connection 1111*a*-1111*b*.

Referring again to FIG. 2 and as discussed above, in one embodiment anode foils 203*a*-203*c* are high formation voltage anode foils. In one embodiment, high formation voltage foils are anode foils having a formation voltage of approximately 441 volts or greater. In one embodiment, the high voltage anode foil comprises an anode foil having a formation voltage between approximately 441 volts and approximately 600 volts. In one embodiment, the high voltage anode foil comprises an anode foil having a formation voltage of approximately 600 volts. In another embodiment, the high voltage anode foil comprises an anode foil having a formation voltage of approximately 600 volts to approximately 880 volts. Other embodiments include other high formation anode foils and will be discussed below. As noted above, some embodiments of the present invention include low and medium formation voltage foil.

Figure 16:
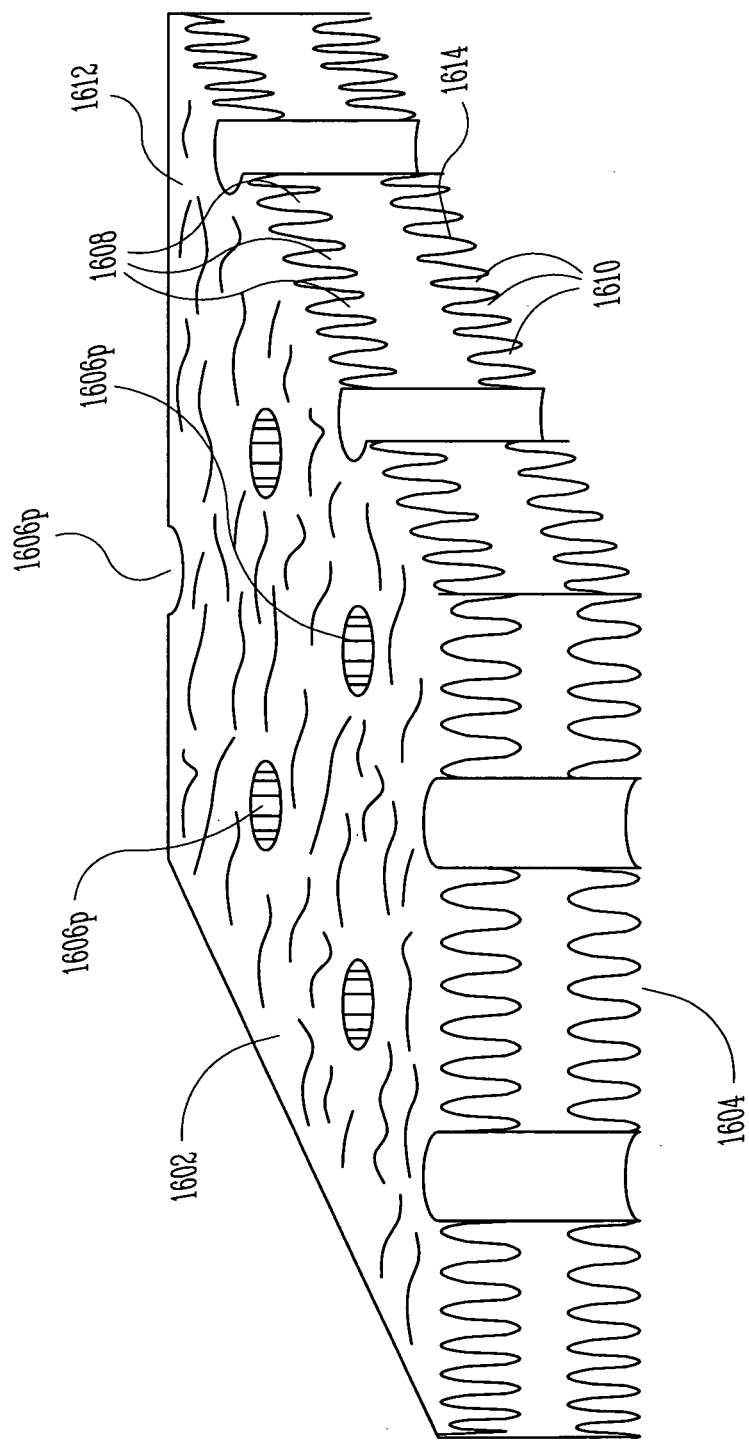
FIG. 16 is an perspective view of an anode foil according to one embodiment of the present invention.

FIG. 16 shows an enlarged perspective view of anode foil 203*a* according to one embodiment of the present invention. Anode 203*a* includes opposing surfaces 1602 and 1604 and a set of perforations 1606*p* which extend through anode foil 203*a* from surface 1602 to surface 1604. Surfaces 1602 and 1604 include respective sets of surface cavities (or depressions) 1608 and 1610, which have generally cylindrical, conical, or hemispherical shapes. However, the anode foils are not limited to any particular cavity form, class of cavity forms, or combination of cavity forms. For instance, some embodiments include a porous structure having only cavities. Some embodiments include only perforations. Other embodiments use tunnel-etched, core-etched, and/or perforated-core-etched foil structures, such as those shown in U.S. patent application Ser. No. 09/165,779 entitled HIGH-ENERGY CAPACITORS FOR IMPLANTABLE DEFIBRILLATORS, which was discussed above. Other embodiments utilize other foil compositions and classes of foil compositions.

On the major surfaces of anode foil 203*a* are oxide layers 1612 and 1614. Oxide layers 1612 and 1614 are the dielectric layers of the capacitor. The dielectric layer separates the anodes from the cathodes. Examples of suitable oxide layers include metallic oxides such as aluminum oxide ($Al_2O_3$). In one embodiment, layers 1612 and 1614 have a thickness sufficient to withstand approximately 441 volts or greater. In one embodiment, layers 1612 and 1614 have a thickness sufficient to withstand up to 600 volts. Other embodiments withstand 600 volts to 800 volts or greater. In one embodiment, dielectric layers 1612 and 1614 have a thickness conforming to and covering the etched surface to a height of at least 540 nm. In some embodiments, the dielectric layer ranges from approximately 573 nm to approximately 1200 nm.

Figure 17:
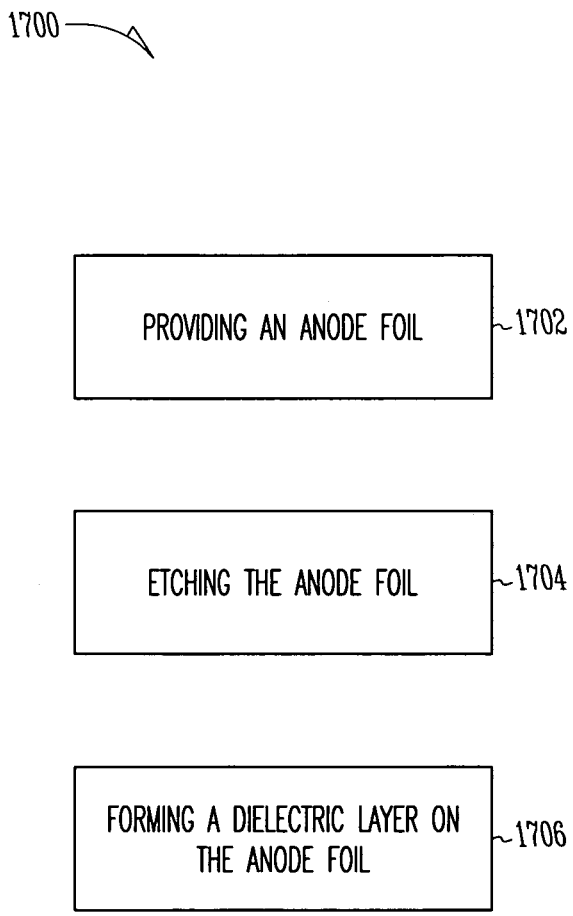
FIG. 17 is a flowchart depicting a method of preparing an anode foil according to one embodiment of the present invention.

FIG. 17 shows a flowchart of a method 1700 for preparing an anode foil for use in a capacitor according to one embodiment of the present invention. In block 1702, the method includes providing an anode foil. In block 1704, the method includes etching the anode foil. In block 1706, the method includes forming a dielectric layer on the anode foil.

In various embodiments, the etching of block 1704 includes core-etching the foil, tunnel-etching the foil, perforating the foil and combinations and permutations of these techniques. In some embodiments, perforations such as perforations 1606*p* discussed above are formed using lasers, chemical etchants, or mechanical dies, for example. Exemplary cavities 1608 and 1610 could also be formed using lasers. Some embodiments tunnel-etch the foil, other embodiments provide other known methods of providing a porous or etched foil. In some embodiments, a porous anode structure is constructed using other roughening or etching techniques.

In one embodiment, forming a dielectric layer comprises forming a layer of $Al_2O_3$ having a thickness in the range of 573 nm to 1200 nm on the anode foil (assuming a dielectric growth rate of 1.3-1.5 nm/V). In one embodiment, the dielectric layer is formed on the anode before the capacitor stack is constructed.

In one embodiment, forming the dielectric layer includes applying a current through the anode and raising the voltage to the rated formation voltage. In one embodiment, the formation voltage is 441 volts. In other embodiments, the forming voltage is 450, 500, 550, 600, and 600-800 volts, and other voltages ranging from approximately 441 to approximately 800 volts or greater. The current causes a dielectric $Al_2O_3$ to form on the surface of the foil. Once the formation voltage is reached, the capacitor is held at that voltage until a leakage current stabilizes at a pre-determined level. By monitoring the rising voltage and/or the leakage current, the oxide formation can be estimated. Once the preset voltage is reached, it plateaus, in which case a current drop ensues in order to balance the increasing resistance of oxide film growth. The process is complete when the current drops to a pre-specified value.

Some embodiments combine etching and dielectric forming so that the etching and dielectric forming are done simultaneously.

In one embodiment, method 1700 results in an aluminum anode foil having a formation voltage between approximately 441 volts and approximately 600 volts. In various embodiment, this includes a foil having a formation voltage of approximately 441, approximately 450, approximately 500, approximately 550, approximately 600, and approximately 600 volts to approximately 800 volts or greater.

Among other advantages, the high formation anode foils described above allow a smaller capacitor to be used within an implantable medical device. In some embodiments, only a single capacitor is needed since it provides enough voltage to perform its necessary function.

EXEMPLARY EMBODIMENT OF
IMPLANTABLE DEFIBRILLATOR

Figure 18:
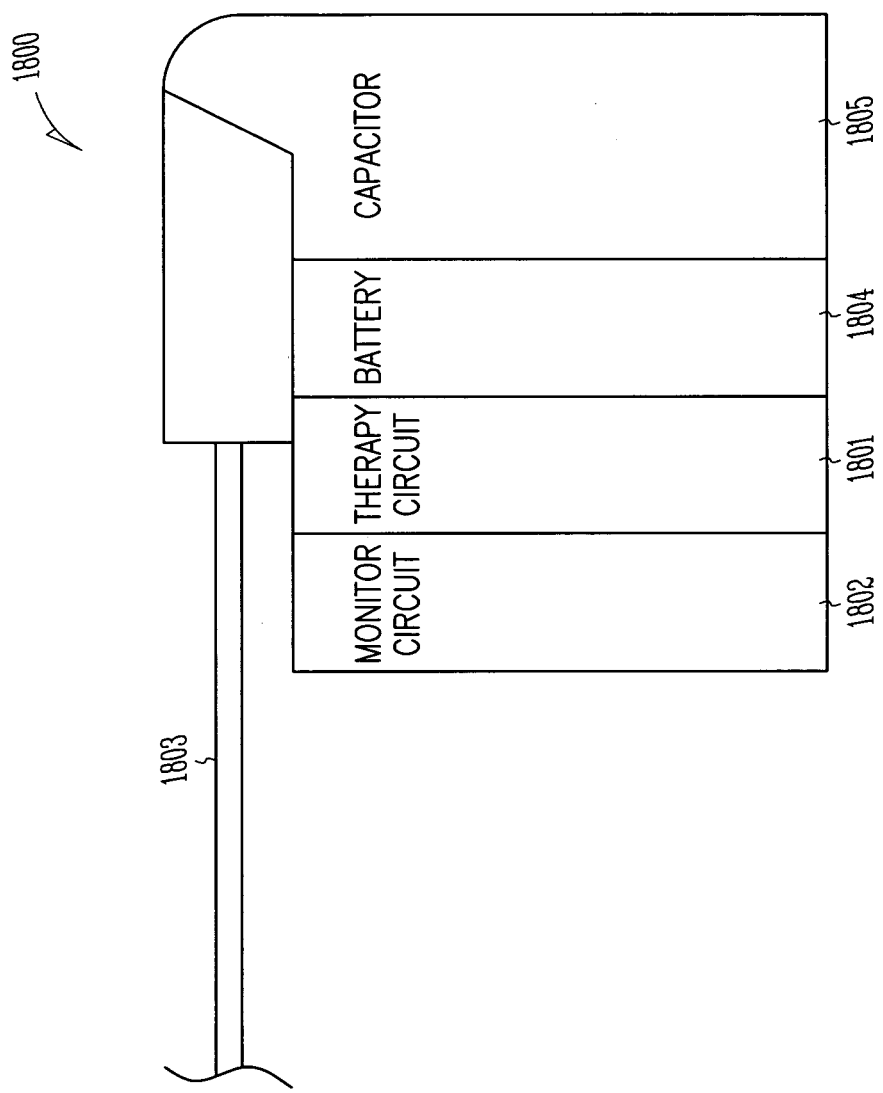
FIG. 18 is a block diagram of a generic implantable medical device including a capacitor according to one embodiment of the present invention.

FIG. 18 shows one of the many applications for capacitors incorporating one or more teachings of the present invention: an implantable medical device or apparatus 1800. As used herein, this includes any implantable device for providing therapeutic stimulus to a heart muscle. Thus, for example, the term includes pacemakers, defibrillators, cardioverters, congestive heart failure devices, and combinations and permutations thereof.

Implantable medical device 1800 includes a lead system 1803, which after implantation electrically contact strategic portions of a patient's heart. Shown schematically are portions of device 1800 including a monitoring circuit 1802 for monitoring heart activity through one or more of the leads of lead system 1803, and a therapy circuit 1801 for delivering electrical energy through one or more of the leads to a heart. Device 1800 also includes an energy storage component, which includes a battery 1804 and incorporates at least one capacitor 1805 having one or more of the features of the exemplary capacitors described above.

In addition to implantable heart monitor and other cardiac rhythm management devices, one or more teachings of the present invention can be incorporated into other flat capacitors, cylindrical capacitors, and capacitors for photographic flash equipment or other applications where high-energy, high-voltage, or space-efficient capacitors are desirable.

CONCLUSION

In furtherance of the art, the inventors have devised foil structures, foil-to-foil connection techniques, connection member-to-connection member joining methods, and connection member-to-foil joining methods, and other methods and structures for a capacitor. One aspect of the present invention includes a method of joining a connection member to a capacitor foil using a staking tool having a tip of less than 0.030" (0.762 mm) in diameter. Another embodiment couples multiple connection members of a capacitor together by edge-connecting each connection member to its substantially flush neighboring connection members. In one aspect, a capacitor includes a multi-anode stack connected at a first weld by a weld joint less than 0.060" (1.524 mm) in diameter and a tab attached to one of the anodes of the multi-anode stack at a second weld. In one aspect, an exemplary method joining one or more foils using a staking tool having a tip of less than approximately 0.060" (1.524 mm) in diameter. In another aspect, a capacitor including a capacitor case having an electrolyte therein and a high formation voltage anode foil having a porous structure and located within the capacitor case.

Among other advantages, the exemplary connection member-to-foil joining method results in a smaller than typical weld joint which permits increased anode brittleness and smaller foil notches. Thus, with all other capacitor factors being equal, it results in a smaller volume capacitor. Other features provide a capacitor which requires less space for its anode connection members and which has a more reliable connection member-to-connection member connection and reduced stress on the connection member-to-foil connection. Among other advantages, the exemplary foil-to-foil joining method permits increased anode brittleness and allows for different permutations of anode foils. Among other advantages, one embodiment provides the high voltages needed for applications such as defibrillation, while the porous foil structure provides for a more space efficient capacitor structure.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:
1. An implantable medical device comprising:
one or more leads for sensing electrical signals of a patient or for applying electrical energy to the patient;
a monitoring circuit for monitoring heart activity of the patient through one or more of the leads; and
a therapy circuit for delivering electrical energy through one or more of the leads to a heart of the patient, wherein the therapy circuit includes a capacitor, the capacitor comprising:
a plurality of anodes, each anode comprising an anode foil having a formation voltage of approximately 441 volts or greater and having a porous structure;
a plurality of cathodes;
a plurality of electrolyte impregnated separators, wherein the capacitor is formed in a stack having alternating anodes and cathodes and at least one of the plurality of electrolyte impregnated separators located between each anode and each cathode;
wherein each of the plurality of anodes includes a separate connection member attached to the anode, the connection member having a first section extending over and confronting a front edge face of the anode, wherein the connection member comprises a main member having a generally L-shaped cross-section; and
and wherein adjacent anodes are stacked so that their respective connection members are positioned in a stacked relationship adjacent to each other such that the outer faces of the adjacent connection members are substantially planar relative to each other.

2. The implantable medical device of claim 1, wherein the anode foil has a formation voltage of approximately 600 volts or higher.

3. The implantable medical device of claim 1, wherein the therapy circuit includes a single capacitor.

4. The implantable medical device of claim 1, wherein each anode foil has a formation voltage of between approximately 441 volts and approximately 600 volts.

5. The implantable medical device of claim 1, wherein each anode foil has a formation voltage of between approximately 600 volts and approximately 800 volts.

6. The implantable medical device of claim 1, wherein the plurality of anode foils comprises a multi-anode stack and wherein, each anode foil of the multi-anode stack is interconnected to the other foils of the multi-anode stack at a stake weld joint having a diameter of less than approximately 0.060" (1.524 mm).

7. The implantable medical device of claim 6, wherein the stake weld has a diameter of approximately 0.025" (0.635 mm).

8. The implantable medical device of claim 6, wherein each of the two or more anode foils comprises a tunnel-etched foil.

9. The implantable medical device of claim 6, wherein each of the anode foils has a formation voltage of between approximately 441 volts and approximately 600 volts.

10. The implantable medical device of claim 6, wherein each of the anode foils has a formation voltage of approximately 600 volts or higher.

11. The implantable medical device of claim 10, wherein each of the anode foils has a formation voltage between approximately 600 volts and approximately 800 volts.

12. The implantable medical device of claim 6, further comprising a second multi-anode stack including two or more anode foils, wherein each anode foil of the second multi-anode stack is connected to the other foils of the second multi-anode stack by a stake weld joint having a diameter less than approximately 0.060" (1.524 mm), and wherein the stake weld joint of the first anode stack is in a different location relative to a major surface of the first multi-anode stack than the stake weld joint of the second multi-anode stack.

13. The implantable medical device of claim 6, wherein the capacitor comprises a flat capacitor.

14. An implantable medical device comprising:
one or more leads for sensing electrical signals of a patient or for applying electrical energy to the patient;
a monitoring circuit for monitoring heart activity of the patient through one or more of the leads; and
a therapy circuit for delivering electrical energy through one or more of the leads to a heart of the patient, wherein the therapy circuit includes one or more capacitors, each capacitor comprising:
a plurality of anodes, each anode having a front edge surface;
a plurality of connection members, wherein each of the plurality of anodes includes one of the plurality of connection members attached to the anode, each connection member comprising a member having an inner surface confronting and abutting the front edge surface of the attached anode, and wherein stacked, adjacent connection members are positioned such that the outer surfaces of the adjacent connection members are substantially planar relative to each other;
a plurality of cathodes; and
a plurality of electrolyte impregnated separators, wherein the capacitor is formed in a stack having alternating anodes and cathodes and at least one of the plurality of electrolyte impregnated separators located between each anode and each cathode.

15. The implantable medical device of claim 14, wherein each anode connection member is connected to each other anode connection member adjacent to each anode connection member by an edge-connection.

16. The implantable medical device of claim 14, wherein each anode connection member is connected to each anode by a stake weld having a diameter of approximately 0.030" (0.762 mm) or less.

17. The implantable medical device of claim 14, wherein at least one of the anodes includes a notch, the connection member having a section fitting within the notch.

18. The implantable medical device of claim 17, wherein the connection member includes a generally L-shaped cross-section.

19. The implantable medical device of claim 18, wherein the L-shaped connection member includes a first section connected to a top surface of the anode and a second section extending over the edge of the anode.

* * * * *